(12) United States Patent
Spencer

(10) Patent No.: US 11,389,628 B2
(45) Date of Patent: Jul. 19, 2022

(54) SUBINTIMAL RE-ENTRY BALLOON CATHETER

(71) Applicant: BOSTON SCIENTIFIC SCIMED, INC., Maple Grove, MN (US)

(72) Inventor: Steven M. Spencer, Minneapolis, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1106 days.

(21) Appl. No.: 15/070,697

(22) Filed: Mar. 15, 2016

(65) Prior Publication Data

US 2016/0271374 A1     Sep. 22, 2016

Related U.S. Application Data

(60) Provisional application No. 62/135,529, filed on Mar. 19, 2015.

(51) Int. Cl.
| | |
|---|---|
| *A61M 25/10* | (2013.01) |
| *A61B 17/22* | (2006.01) |
| *A61M 25/01* | (2006.01) |

(52) U.S. Cl.
CPC ............ *A61M 25/104* (2013.01); *A61B 17/22* (2013.01); *A61M 25/0194* (2013.01);
(Continued)

(58) Field of Classification Search
CPC ......... A61B 2017/22095; A61B 2017/320048; A61B 17/8855; A61B 2017/22069; A61B 2017/22071; A61B 17/22; A61B 2017/22001; A61B 2017/22045; A61B 2017/22062; A61B 2017/22065; A61M 25/104; A61M 2025/0197; A61M 25/10;
(Continued)

(56) References Cited

U.S. PATENT DOCUMENTS

| | | |
|---|---|---|
| 4,927,412 A | 5/1990 | Menasche |
| 5,690,642 A | 11/1997 | Osborne et al. |

(Continued)

FOREIGN PATENT DOCUMENTS

| | | |
|---|---|---|
| WO | 9744083 A1 | 11/1997 |
| WO | 2009100129 A2 | 8/2009 |

(Continued)

*Primary Examiner* — Anh T Dang
(74) *Attorney, Agent, or Firm* — Seager, Tufte & Wickhem LLP

(57) ABSTRACT

A balloon catheter including a catheter shaft and an inflatable balloon secured to a distal end region of the catheter shaft. The inflatable balloon has a generally conical shape in a fully inflated configuration having a proximal conical portion that tapers away from the central longitudinal axis in a distal direction from a proximal waist of the balloon and a distal conical portion that tapers toward the central longitudinal axis in a distal direction toward a distal waist of the balloon, with a radially outermost extent of the balloon located between the proximal conical portion and the distal conical portion. The proximal conical portion, the distal conical portion and/or the radially outermost extent of the balloon has an elliptical cross-section taken in a plane perpendicular to the central longitudinal axis of the catheter shaft.

20 Claims, 16 Drawing Sheets

(52) U.S. Cl.
CPC ............... *A61M 25/1002* (2013.01); *A61B 2017/22001* (2013.01); *A61B 2017/22045* (2013.01); *A61B 2017/22062* (2013.01); *A61B 2017/22065* (2013.01); *A61M 2025/0197* (2013.01); *A61M 2025/1065* (2013.01)

(58) Field of Classification Search
CPC .......... A61M 25/1002; A61M 25/1006; A61M 2025/1059; A61M 2025/1065; A61M 25/0194; A61M 25/1034; A61M 2025/1061; B29L 2031/7543; A61F 2002/30125; A61F 2002/30126; A61F 2002/30128; A61F 2002/30205; A61F 2002/30228; A61F 2002/30253; A61F 2230/0076

See application file for complete search history.

(56) References Cited

U.S. PATENT DOCUMENTS

| | | | |
|---|---|---|---|
| 5,814,061 | A | 9/1998 | Osborne et al. |
| 5,830,222 | A | 11/1998 | Makower et al. |
| 5,935,108 | A | 8/1999 | Katoh et al. |
| 5,938,671 | A | 8/1999 | Katoh et al. |
| 5,968,064 | A | 10/1999 | Selmon et al. |
| 5,972,015 | A * | 10/1999 | Scribner ............... A61B 10/025 604/20 |
| 6,010,449 | A | 1/2000 | Selmon et al. |
| 6,068,638 | A | 5/2000 | Makower et al. |
| 6,120,516 | A | 9/2000 | Selmon et al. |
| 6,129,737 | A * | 10/2000 | Hamilton .......... A61M 25/1002 604/916 |
| 6,159,225 | A | 12/2000 | Makower et al. |
| 6,190,353 | B1 | 2/2001 | Makower et al. |
| 6,217,527 | B1 | 4/2001 | Selmon et al. |
| 6,217,549 | B1 | 4/2001 | Selmon et al. |
| 6,221,049 | B1 | 4/2001 | Selmon et al. |
| 6,231,546 | B1 | 5/2001 | Milo et al. |
| 6,231,587 | B1 | 5/2001 | Makower |
| 6,235,000 | B1 | 5/2001 | Milo et al. |
| 6,241,667 | B1 | 6/2001 | Vetter et al. |
| 6,371,961 | B1 | 4/2002 | Osborne et al. |
| 6,398,798 | B2 | 6/2002 | Selmon et al. |
| 6,506,178 | B1 | 1/2003 | Schubart et al. |
| 6,508,825 | B1 | 1/2003 | Selmon et al. |
| 6,511,458 | B2 | 1/2003 | Milo et al. |
| 6,514,217 | B1 | 2/2003 | Selmon et al. |
| 6,579,302 | B2 | 6/2003 | Duerig et al. |
| 6,599,304 | B1 | 7/2003 | Selmon et al. |
| 6,632,235 | B2 * | 10/2003 | Weikel ................ A61B 17/025 606/192 |
| 6,638,247 | B1 | 10/2003 | Selmon et al. |
| 6,663,577 | B2 | 12/2003 | Jen et al. |
| 6,709,444 | B1 | 3/2004 | Makower |
| 6,719,725 | B2 | 4/2004 | Milo et al. |
| 6,955,175 | B2 | 10/2005 | Stevens et al. |
| 6,979,290 | B2 * | 12/2005 | Mourlas ............. A61B 1/00082 600/104 |
| 7,004,173 | B2 | 2/2006 | Sparks et al. |
| 7,105,031 | B2 * | 9/2006 | Letort .................... A61F 2/954 128/898 |
| 7,179,270 | B2 | 2/2007 | Makower |
| 7,229,421 | B2 | 6/2007 | Jen et al. |
| 7,357,794 | B2 | 4/2008 | Makower et al. |
| 7,666,205 | B2 * | 2/2010 | Weikel ................ A61B 17/025 606/192 |
| 7,740,623 | B2 | 6/2010 | Nayak et al. |
| 7,771,462 | B1 | 8/2010 | Davidson et al. |
| 7,918,859 | B2 | 4/2011 | Katoh et al. |
| 7,918,870 | B2 | 4/2011 | Kugler et al. |
| 7,938,819 | B2 | 5/2011 | Kugler et al. |
| 7,993,343 | B2 * | 8/2011 | Lin .................... A61B 17/3431 604/500 |
| 8,025,655 | B2 | 9/2011 | Kugler et al. |
| 8,083,727 | B2 | 12/2011 | Kugler et al. |
| 8,172,863 | B2 | 5/2012 | Robinson et al. |
| 8,202,246 | B2 | 6/2012 | Kugler et al. |
| 8,323,261 | B2 | 12/2012 | Kugler et al. |
| 8,337,425 | B2 | 12/2012 | Olson et al. |
| 8,512,310 | B2 | 8/2013 | Kugler et al. |
| 8,721,675 | B2 * | 5/2014 | Rottenberg ............ A61B 17/02 606/194 |
| 8,961,553 | B2 * | 2/2015 | Hollowell .......... A61B 17/7098 604/264 |
| 9,446,222 | B2 * | 9/2016 | Silvestro ............... A61M 29/02 |
| 9,533,125 | B2 * | 1/2017 | Connolly .......... A61M 25/1029 |
| 2001/0000041 | A1 | 3/2001 | Selmon et al. |
| 2001/0012924 | A1 | 8/2001 | Milo et al. |
| 2002/0103459 | A1 | 8/2002 | Sparks et al. |
| 2002/0128677 | A1 | 9/2002 | Duerig et al. |
| 2003/0109809 | A1 | 6/2003 | Jen et al. |
| 2003/0109909 | A1 | 6/2003 | Ledesma et al. |
| 2003/0120195 | A1 | 6/2003 | Milo et al. |
| 2003/0139763 | A1 | 7/2003 | Duerig et al. |
| 2004/0167554 | A1 | 8/2004 | Simpson et al. |
| 2004/0230219 | A1 | 11/2004 | Roucher, Jr. |
| 2005/0015048 | A1 * | 1/2005 | Chiu .................... A61M 25/10 604/101.04 |
| 2005/0075662 | A1 | 4/2005 | Pedersen et al. |
| 2005/0149062 | A1 | 7/2005 | Carroll |
| 2005/0171478 | A1 | 8/2005 | Selmon et al. |
| 2006/0094930 | A1 | 5/2006 | Sparks et al. |
| 2006/0167437 | A1 | 7/2006 | Valencia |
| 2006/0167554 | A1 | 7/2006 | Heck et al. |
| 2006/0184011 | A1 | 8/2006 | Macaulay et al. |
| 2006/0230219 | A1 | 10/2006 | Njoku et al. |
| 2006/0276749 | A1 | 12/2006 | Selmon et al. |
| 2007/0010787 | A1 * | 1/2007 | Hackett ............... A61M 25/005 604/96.01 |
| 2007/0093779 | A1 | 4/2007 | Kugler et al. |
| 2007/0093780 | A1 | 4/2007 | Kugler et al. |
| 2007/0093781 | A1 | 4/2007 | Kugler et al. |
| 2007/0093782 | A1 | 4/2007 | Kugler et al. |
| 2007/0208368 | A1 | 9/2007 | Katoh et al. |
| 2007/0265596 | A1 | 11/2007 | Jen et al. |
| 2008/0033423 | A1 | 2/2008 | Peacock |
| 2008/0125748 | A1 | 5/2008 | Batel |
| 2008/0125760 | A1 * | 5/2008 | Gilboa .................. A61M 25/04 604/892.1 |
| 2008/0154172 | A1 | 6/2008 | Mauch |
| 2008/0200896 | A1 | 8/2008 | Shmulewitz et al. |
| 2008/0228171 | A1 | 9/2008 | Kugler et al. |
| 2008/0243065 | A1 * | 10/2008 | Rottenberg ......... A61M 25/104 604/96.01 |
| 2008/0243067 | A1 * | 10/2008 | Rottenberg ............ A61B 17/02 604/99.01 |
| 2008/0249397 | A1 | 10/2008 | Kapadia |
| 2008/0294103 | A1 | 11/2008 | Pereira |
| 2008/0306499 | A1 | 12/2008 | Katoh et al. |
| 2009/0005755 | A1 | 1/2009 | Keith et al. |
| 2009/0088685 | A1 | 4/2009 | Kugler et al. |
| 2009/0093791 | A1 | 4/2009 | Heuser |
| 2009/0099515 | A1 * | 4/2009 | Quilter ............... A61M 25/1002 604/96.01 |
| 2009/0124899 | A1 | 5/2009 | Jacobs et al. |
| 2009/0209910 | A1 | 8/2009 | Kugler et al. |
| 2009/0230167 | A1 | 9/2009 | Xiao et al. |
| 2009/0254107 | A1 | 10/2009 | Katoh et al. |
| 2009/0264826 | A1 | 10/2009 | Thompson |
| 2009/0292296 | A1 | 11/2009 | Pansky et al. |
| 2009/0299171 | A1 | 12/2009 | Duffy et al. |
| 2009/0299402 | A1 | 12/2009 | Orihashi et al. |
| 2010/0063534 | A1 * | 3/2010 | Kugler ................. A61B 17/221 606/200 |
| 2010/0067745 | A1 | 3/2010 | Kovtun et al. |
| 2010/0069945 | A1 | 3/2010 | Olson et al. |
| 2010/0125244 | A1 | 5/2010 | McAndrew |
| 2010/0317973 | A1 | 12/2010 | Nita |
| 2011/0112564 | A1 | 5/2011 | Wolf |
| 2011/0144677 | A1 | 6/2011 | Ward et al. |
| 2011/0166591 | A1 | 7/2011 | Katoh et al. |

(56) References Cited

U.S. PATENT DOCUMENTS

| | | | |
|---|---|---|---|
| 2012/0323269 A1* | 12/2012 | Rottenberg | A61B 17/02 |
| | | | 606/194 |
| 2013/0006282 A1 | 1/2013 | Wilkinson | |
| 2013/0072957 A1* | 3/2013 | Anderson | A61M 25/104 |
| | | | 606/194 |
| 2013/0317534 A1* | 11/2013 | Zhou | A61B 17/3207 |
| | | | 606/185 |
| 2014/0200603 A1 | 7/2014 | Zhou et al. | |
| 2014/0277053 A1* | 9/2014 | Wang | A61M 25/0194 |
| | | | 606/185 |
| 2015/0250991 A1* | 9/2015 | Silvestro | A61M 29/02 |
| | | | 606/194 |

FOREIGN PATENT DOCUMENTS

| | | |
|---|---|---|
| WO | 2011025855 A2 | 3/2011 |
| WO | 2013003194 A1 | 1/2013 |

* cited by examiner

SUBINTIMAL RE-ENTRY BALLOON CATHETER

CROSS REFERENCE TO RELATED APPLICATIONS

The present application claims the benefit of and priority to U.S. Provisional Patent Application No. 62/135,529, filed Mar. 19, 2015, the disclosure of which is incorporated herein by reference.

TECHNICAL FIELD

The disclosure is directed to devices and methods for recanalization of an occluded blood vessel. More particularly, the disclosure is directed to devices and methods for re-entry into the true lumen from the extraluminal or subintimal space of a blood vessel.

BACKGROUND

Chronic total occlusion (CTO) is an arterial vessel blockage that obstructs blood flow through the vessel, and can occur in both coronary and peripheral arteries. In some instances, it may be difficult or impossible to pass through the CTO with a medical device in an antegrade direction to recanalize the vessel. Accordingly, techniques have been developed for creating a subintimal pathway (i.e., a pathway between the intimal and adventitial tissue layers of the vessel) around the occlusion and then re-entering the true lumen of the vessel distal of the occlusion in an attempt to recanalize the vessel. In some instances re-entering the true lumen from the subintimal space and/or recanalization can be difficult. Accordingly, it is desirable to provide alternative recanalization devices and/or methods of recanalizing a blood vessel in which a CTO is present.

BRIEF SUMMARY

The disclosure is directed to several alternative designs, materials and methods of manufacturing medical device structures and assemblies, and uses thereof.

One example is a balloon catheter including a catheter shaft having a central longitudinal axis, a guidewire lumen and an inflation lumen extending therethrough. The balloon catheter also includes an inflatable balloon secured to a distal end region of the catheter shaft. The inflatable balloon has a proximal waist secured to the catheter shaft and a distal waist secured to the catheter shaft. The inflatable balloon has a generally conical shape having a proximal conical portion that tapers radially outward (e.g., away from the central longitudinal axis) in a distal direction from the proximal waist. The proximal conical portion has an elliptical cross-section taken in a plane perpendicular to the central longitudinal axis that passes through the proximal conical portion.

Alternatively or additionally to any of the embodiments above, the inflatable balloon has a distal conical portion and a radially outermost extent between the proximal conical portion and the distal conical portion and the distal conical portion has an elliptical cross-section taken in a plane perpendicular to the central longitudinal axis that passes through the distal conical portion.

Alternatively or additionally to any of the embodiments above, the distal conical portion tapers radially inward (e.g., toward the central longitudinal axis) in a distal direction toward the distal waist.

Alternatively or additionally to any of the embodiments above, the proximal conical portion has a first length measured along the central longitudinal axis from the proximal waist to the radially outermost extent and the distal conical portion has a second length measured along the central longitudinal axis from the radially outermost extent to a distal tip of the balloon. The first length is greater than the second length.

Alternatively or additionally to any of the embodiments above, the proximal conical portion tapers away from the central longitudinal axis at a first angle in a first plane parallel to and passing through the central longitudinal axis, and the proximal conical portion tapers away from the central longitudinal axis at a second angle in a second plane parallel to and passing through the central longitudinal axis. The second plane is perpendicular to the first plane and the first angle is greater than the second angle.

Alternatively or additionally to any of the embodiments above, the distal conical portion tapers toward the central longitudinal axis at a third angle in the first plane parallel to and passing through the central longitudinal axis, and the distal conical portion tapers toward the central longitudinal axis at a fourth angle in the second plane parallel to and passing through the central longitudinal axis. The third angle is greater than the fourth angle.

Alternatively or additionally to any of the embodiments above, the first angle is less than the fourth angle.

Alternatively or additionally to any of the embodiments above, the first angle is greater than the fourth angle.

Alternatively or additionally to any of the embodiments above, the balloon is located a first distance from the central longitudinal axis in a first direction taken in a plane perpendicular to the central longitudinal axis that passes through the radially outermost extent, and the balloon is located a second distance from the central longitudinal axis in a second direction taken in the plane perpendicular to the central longitudinal axis that passes through the radially outermost extent. The second direction is perpendicular to the first direction and the first distance is less than the second distance.

Alternatively or additionally to any of the embodiments above, the distal waist is an inverted distal waist secured to the catheter shaft.

Alternatively or additionally to any of the embodiments above, the inflatable balloon is only secured to the catheter shaft at the proximal and distal waists.

Alternatively or additionally to any of the embodiments above, a distalmost extent of the inflatable balloon is flush with or extends distal of a distal end of the catheter shaft in an inflated configuration.

Alternatively or additionally to any of the embodiments above, the catheter shaft includes an inner tubular member defining the guidewire lumen and an outer tubular member extending around the inner tubular member. The inflation lumen is defined between the inner tubular member and the outer tubular member. The proximal waist is secured to a distal end region of the outer tubular member and the distal waist is secured to a distal end region of the inner tubular member.

Another example is a subintimal recanalization catheter assembly for recanalizing a blood vessel having an occlusion in a lumen thereof. The catheter assembly includes an elongate catheter shaft having a central longitudinal axis and an inflatable balloon. The catheter shaft includes an outer tubular member having a lumen extending therethrough and an inner tubular member having a lumen extending therethrough. The inner tubular member is disposed in the lumen of the outer tubular member. The inflatable balloon has a proximal waist secured to a distal end region of the outer tubular member and a distal waist secured to a distal end region of the inner tubular member. The inflatable balloon is configured to be inflated from an uninflated configuration to an inflated configuration with an inflation fluid. A distalmost extent of the inflatable balloon is flush with or extends distal of a distal end of the catheter shaft in the inflated configuration. The inflatable balloon has an elliptical cross-section taken in a plane perpendicular to the central longitudinal axis that passes through the inflatable balloon.

Alternatively or additionally to any of the embodiments above, the inflatable balloon has a generally conical shape having a proximal conical portion that tapers away from the central longitudinal axis in a distal direction from the proximal waist.

Alternatively or additionally to any of the embodiments above, the inflatable balloon has a distal conical portion and a radially outermost extent between the proximal conical portion and the distal conical portion.

Alternatively or additionally to any of the embodiments above, the proximal conical portion has an elliptical cross-section taken in a plane perpendicular to the central longitudinal axis that passes through the proximal conical portion and the distal conical portion has an elliptical cross-section taken in a plane perpendicular to the central longitudinal axis that passes through the distal conical portion.

Alternatively or additionally to any of the embodiments above, the distal conical portion tapers toward the central longitudinal axis in a distal direction toward the distal waist.

Another example is a method of forming a catheter. The method includes forming an inflatable balloon having a proximal waist and a distal waist. The inflatable balloon has a generally conical shape having a proximal conical portion that tapers radially outward in a distal direction from the proximal waist. The proximal conical portion has an elliptical cross-section. The method further includes securing the inflatable balloon to a distal end region of a catheter shaft with the proximal waist of the inflatable balloon secured to the catheter shaft and the distal waist of the inflatable balloon secured to the catheter shaft.

Alternatively or additionally to any of the embodiments above, the inflatable balloon has a distal conical portion and a radially outermost extent between the proximal conical portion and the distal conical portion. The distal conical portion has an elliptical cross-section. The distal conical portion tapers radially inward in a distal direction toward the distal waist.

Another example is a method of recanalizing a blood vessel having an occlusion in a lumen thereof. The method includes advancing an inflatable balloon secured to a distal end region of a catheter shaft into a subintimal space between a first tissue layer and a second tissue layer of a wall of a vessel such that the inflatable balloon is positioned in the subintimal space distal to the occlusion. Thereafter, the method includes inflating the inflatable balloon to an inflated configuration within the subintimal space. In the inflated configuration the inflatable balloon has a generally conical shape having a proximal conical portion that tapers radially outward (e.g., away from a central longitudinal axis of the catheter shaft) in a distal direction from a proximal waist of the inflatable balloon. The proximal conical portion has an elliptical cross-section taken in a plane perpendicular to a central longitudinal axis of the catheter shaft that passes through the proximal conical portion. The method further includes advancing a penetration member through the catheter shaft such that the penetration member extends distally from the inflatable balloon through the first tissue layer into the lumen of the blood vessel.

Alternatively or additionally to any of the embodiments above, the inflatable balloon has a distal conical portion and a radially outermost extent between the proximal conical portion and the distal conical portion. The distal conical portion tapers radially inward (e.g., toward the central longitudinal axis) in a distal direction toward a distal waist of the inflatable balloon. The distal conical portion has an elliptical cross-section taken in a plane perpendicular to the central longitudinal axis that passes through the distal conical portion.

The above summary of some example embodiments is not intended to describe each disclosed embodiment or every implementation of the aspects of the disclosure.

BRIEF DESCRIPTION OF THE DRAWINGS

The aspects of the disclosure may be further understood in consideration of the following detailed description of various embodiments in connection with the accompanying drawings, in which.

Figure 1:
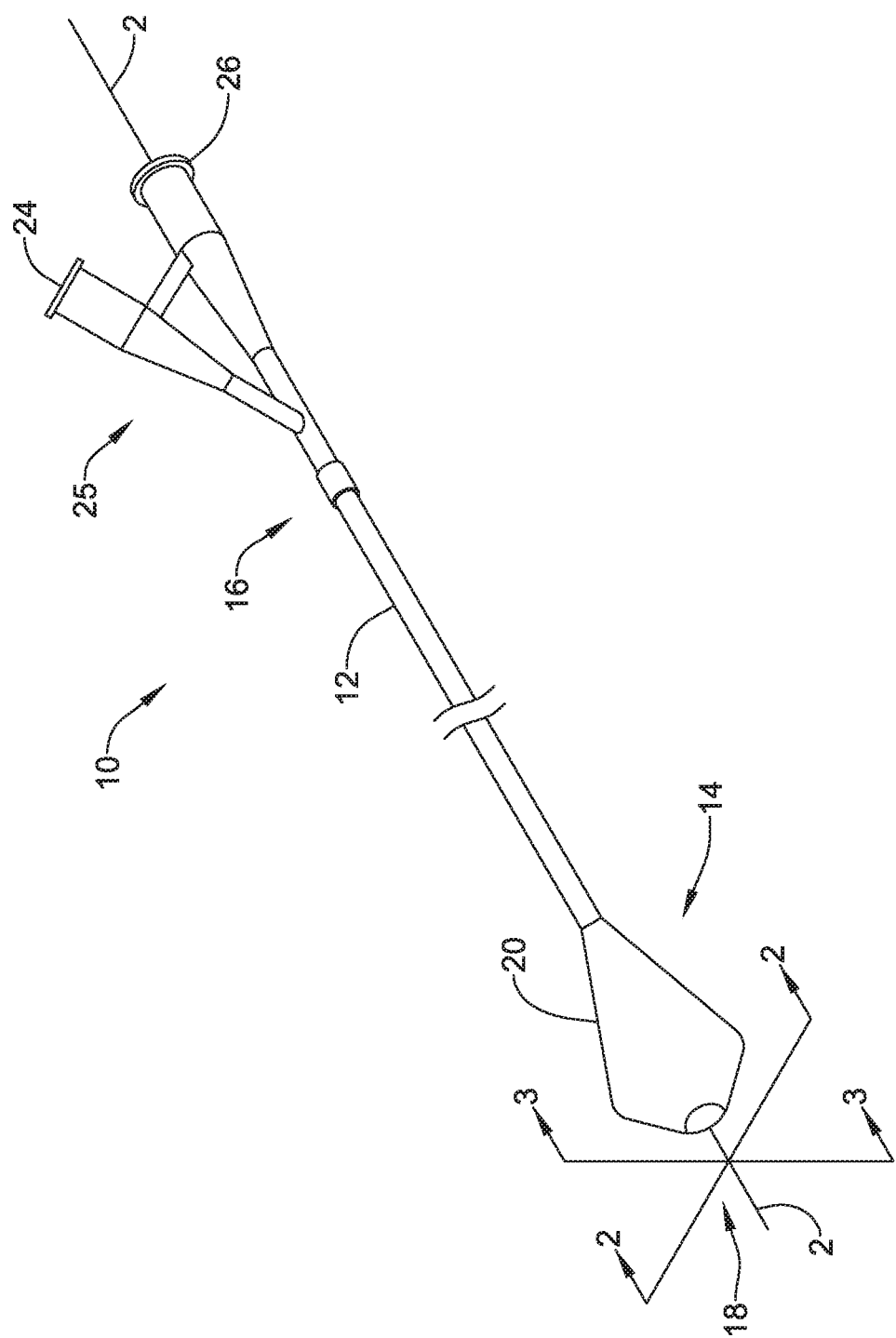
FIG. 1 is a perspective view of an exemplary balloon catheter in accordance with the disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary balloon catheter 10 is illustrated at FIG. 1. The balloon catheter 10 may include a catheter shaft 12 extending from a hub assembly 25 at a proximal end 16 of the catheter shaft 12 to an inflatable balloon 20 mounted on a distal end region of the catheter shaft 12 proximate the distal end 14 of the catheter shaft 12. In some instances, the balloon catheter 10 may be used as a recanalization catheter for recanalizing an occluded blood vessel via a subintimal approach.

The catheter 10 may be configured to be advanced over a guidewire 2 for delivery to a remote location in the vasculature of a patient. For example, in some instances the catheter 10 may be configured as an over-the-wire (OTW) catheter having a guidewire lumen 22 (see FIGS. 2 and 3) extending through the entire length of the catheter 10 from a distal opening or port 29 at a distal tip 18 of the catheter 10 to a proximal guidewire port 26 in the hub assembly 25. In other instances, the catheter 10 may be configured as a single-operator-exchange (SOE) catheter having a guidewire lumen 22 extending from the distal port 29 to a proximal guidewire port (not shown) located a short distance proximal of the inflatable balloon 20 and distal of the hub assembly 25. In such a configuration, the guidewire 2 may extend through the guidewire lumen 22 between the distal opening or port 29 and the proximal port, and extend along an exterior of the catheter shaft 12 proximal of the proximal port to the proximal end 16 of the catheter shaft 12. It is noted that in instances in which the catheter 10 is an SOE catheter, the hub assembly 25 may not include a proximal guidewire port 26.

The catheter shaft 12 may also include an inflation lumen 28 (see FIGS. 2 and 3) in fluid communication with the inflatable balloon 20 configured to deliver an inflation fluid to the inflatable balloon 20 to inflate the inflatable balloon 20 and/or withdraw an inflation fluid from the inflatable balloon to deflate the inflatable balloon 20 during use. The inflation lumen 28 may extend from an inflation port 24 in the hub assembly 25, through the catheter shaft 12 to the interior of the inflatable balloon 20.

Figure 2:
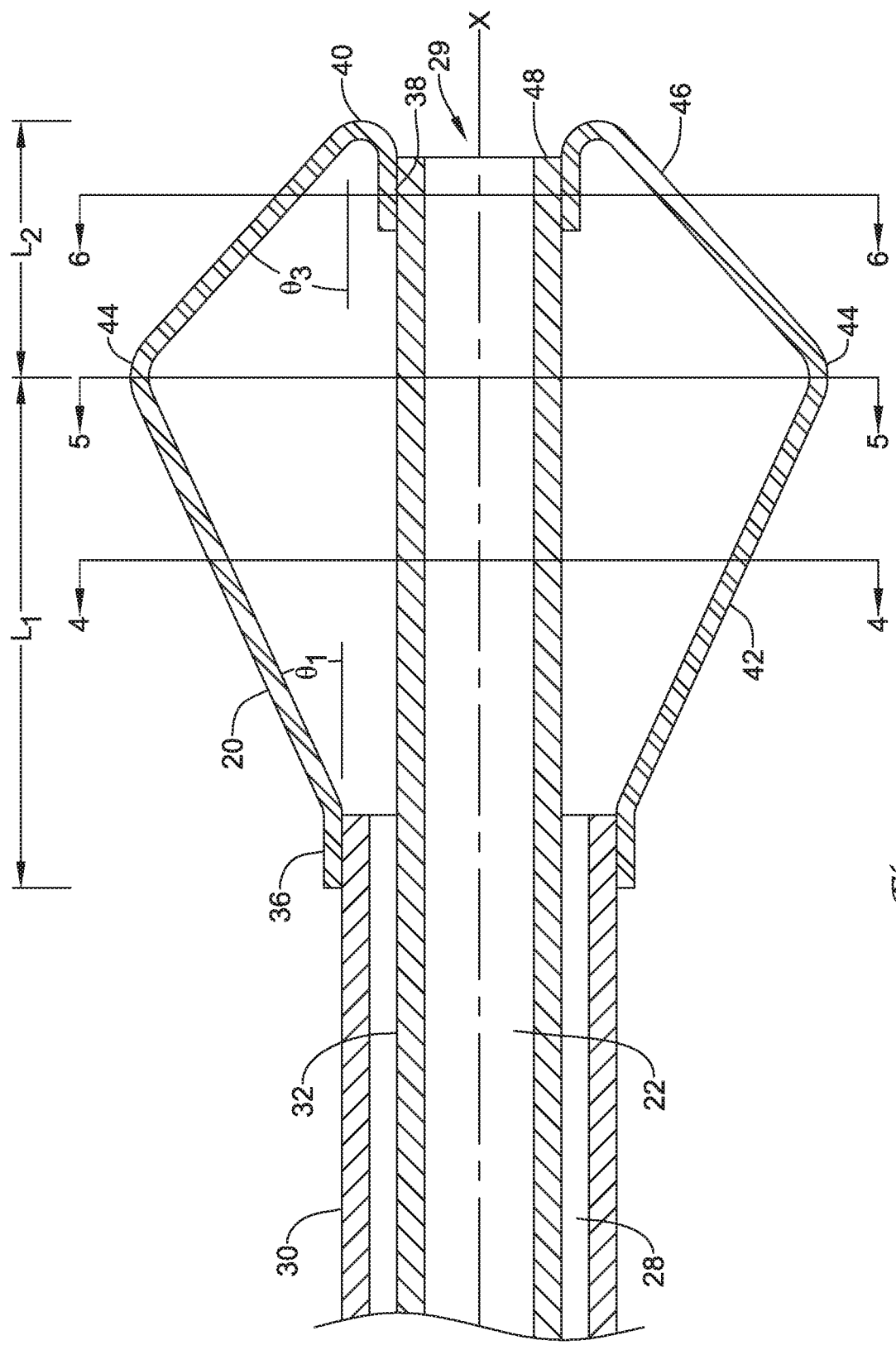
FIG. 2 is a longitudinal cross-sectional view of the distal end region of the balloon catheter of FIG. 1 taken along line 2-2.
Figure 3:
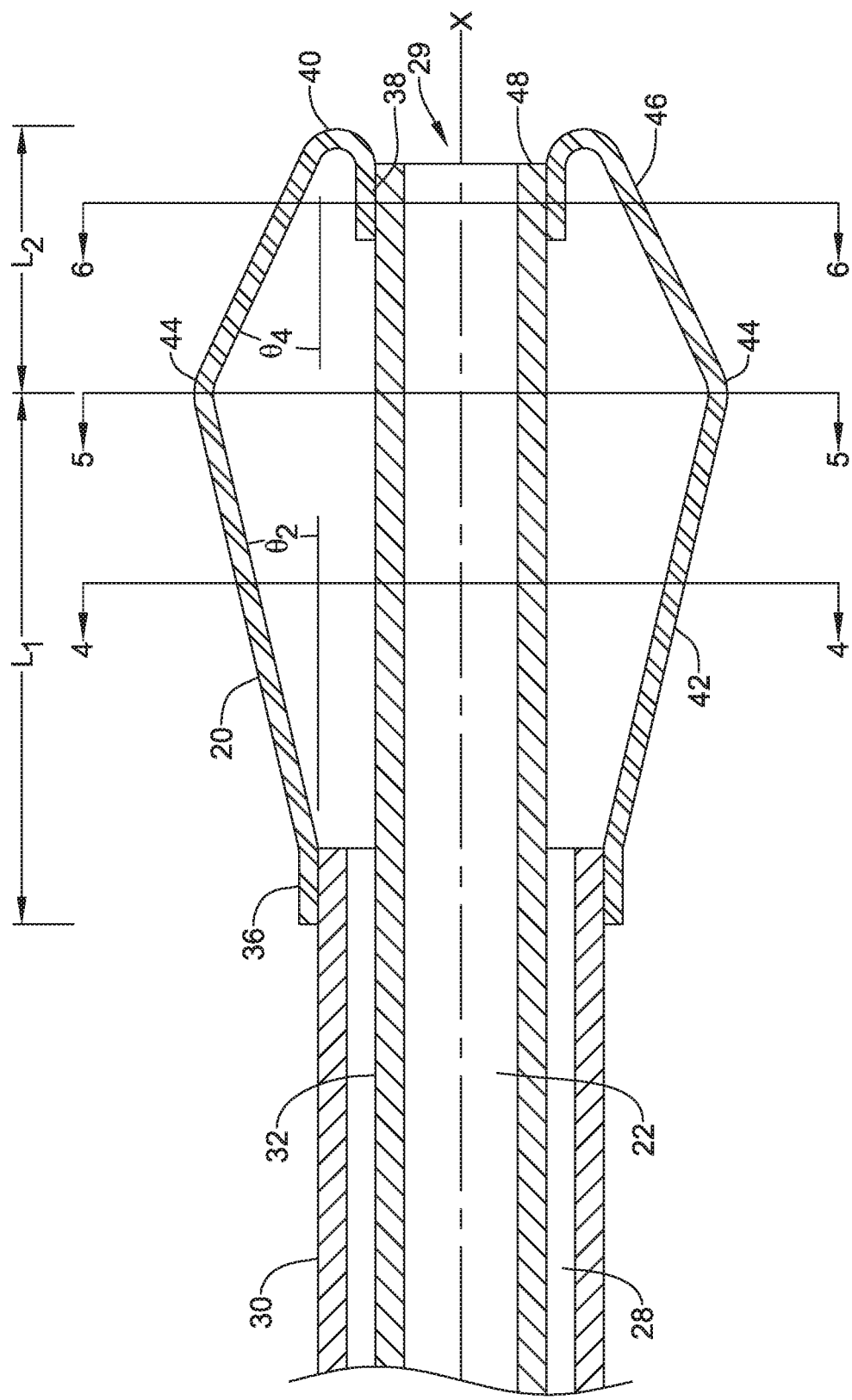
FIG. 3 is a longitudinal cross-sectional view of the distal end region of the balloon catheter of FIG. 1 taken along line 3-3.

The catheter shaft 12 may have a central longitudinal axis X. The catheter shaft 12 may be formed of any desired construction, having the guidewire lumen 22, the inflation lumen 28, and/or one or more additional lumens extending therethrough, if desired. For example, as shown in FIGS. 2 and 3, the catheter shaft 12 may include an outer tubular member 30 and an inner tubular member 32 extending through the lumen of the outer tubular member 30. In such a construction, the lumen of the inner tubular member 32, e.g., the guidewire tube, may define the guidewire lumen 22, and the space between the inner surface of the outer tubular member 30 and the outer surface of the inner tubular member 32 may define the inflation lumen 28. In some instances, the inner tubular member 32 may extend coaxially with the outer tubular member 30 along the central longitudinal axis X, with the annular space formed therebetween defining the inflation lumen 28. The inner tubular member 32 may extend distal of the distal end of the outer tubular member 30, with the proximal waist 36 of the inflatable balloon 20 secured to the distal end of the outer tubular member 30 and the distal waist 38 of the inflatable balloon 20 secured to the distal end of the inner tubular member 32 proximate the distal tip of the catheter shaft 12. Accordingly, the inner tubular member 32, e.g., the guidewire tube, may extend through the interior of the inflatable balloon 20.

The outer tubular member 30 and/or the inner tubular member 32 may be an extruded tubular member formed during an extrusion process. In some instances, the outer tubular member 30 and/or the inner tubular member 32 may be a single layer extruded tube formed of a single layer of polymeric material. In other instances, the outer tubular member 30 and/or the inner tubular member 32 may be a multilayer extruded tube formed of multiple layers of polymeric materials. For example, the outer tubular member 30 and/or the inner tubular member 32 may include two, three, or more discrete layers of different polymer materials and/or compositions.

In other instances, the catheter shaft 12, or portions thereof, may be an extruded shaft having the guidewire lumen 22, the inflation lumen 28, and/or one or more additional lumens formed therein. In such instances, the guidewire tube defining the guidewire lumen 22 may extend through the interior of the inflatable balloon 20.

The balloon 20 may include a proximal waist 36 bonded, for example thermally bonded (e.g., laser, hot jaws) or adhesively bonded to a component of the catheter shaft 12. For example, the proximal waist 36 of the balloon 20 may be bonded or secured to the distal end of the outer tubular member 30. The balloon 20 may also include a distal waist 38 bonded, for example thermally bonded (e.g., laser, hot jaws) or adhesively bonded to a component of the catheter shaft 12. For example, the distal waist 38 of the balloon 20 may be bonded or secured to the distal end of the inner tubular member 32. The balloon 20 may only be secured to the catheter shaft 12 (e.g., inner tubular member 32 and outer tubular member 30) at the proximal and distal balloon waists 36, 38.

As shown in FIGS. 2 and 3, the distal waist 38 may be inverted (e.g., extend proximally from the distal balloon tip 40) such that an inflatable portion of the balloon 20 is located at the distalmost extent of the catheter 10. Thus, the distal tip 40 of the balloon 20, which may be an inflatable portion of the balloon 20, may be positioned at (flush with) or distal of the distal end 48 of the inner tubular member 32 and distal of the distal waist 38 of the balloon 20.

The inflatable balloon 20 may have a generally conical shape in a fully inflated configuration. For example, the inflatable balloon 20 may have a proximal conical portion 42 that tapers away from the central longitudinal axis X in a distal direction from the proximal waist 36. The proximal conical portion 42 may taper radially outward from the central longitudinal axis X in a distal direction to a radially outermost extent 44 of the inflatable balloon 20. The inflatable balloon 20 may also have a distal conical portion 46 that tapers toward the central longitudinal axis X in a distal direction toward the distal waist 38, with the radially outermost extent 44 located between the proximal conical portion 42 and the distal conical portion 46.

The proximal conical portion 42 may have a first length $L_1$ measured along the central longitudinal axis X from the proximal waist 36 to the radially outermost extent 44 and the distal conical portion 46 may have a second length $L_2$ measured along the central longitudinal axis X from the radially outermost extent 44 to the distal tip 40 (i.e., distalmost extent) of the inflatable balloon 20. In some instances, the first length $L_1$ may be equal to the second length $L_2$, or the first length $L_1$ may be different from the second length $L_2$. For instance, the first length $L_1$ may be greater than or less than the second length $L_2$. In the illustrated embodiment, the first length $L_1$ is greater than the second length $L_2$, such that the outermost extent 44 of the inflatable balloon 20 is located closer to the distal tip 40 (i.e., distalmost extent) of the inflatable balloon 20 than the proximal waist 36 of the inflatable balloon 20. In some instances, the first length $L_1$ may about 1 mm to about 30 mm, about 1 mm to about 20 mm, 2 mm to about 15 mm, about 5 mm to about 20 mm, or about 5 mm to about 15 mm, for example. In some instances, the second length $L_2$ may about 1 mm to about 30 mm, about 1 mm to about 20 mm, 2 mm to about 15 mm, about 5 mm to about 20 mm, or about 5 mm to about 15 mm, for example FIG. 2, which is a longitudinal cross-sectional view taken along line 2-2 in FIG. 1, shows the cross-section of the inflatable balloon 20 in a first plane parallel to and passing through the central longitudinal axis X of the catheter shaft 12. FIG. 3, which is a longitudinal cross-sectional view taken along line 3-3 in FIG. 1, shows the cross-section of the inflatable balloon 20 in a second plane parallel to and passing through the central longitudinal axis X of the catheter shaft 12 which is perpendicular to the first plane shown in FIG. 2.

The proximal conical portion 42 may taper away from the central longitudinal axis X at a first angle $\theta_1$ in the first plane (FIG. 2) and the proximal conical portion 42 may taper away from the central longitudinal axis X at a second angle $\theta_2$ in the second plane (FIG. 3) different from the first angle $\theta_1$. In the illustrated embodiment, the first angle $\theta_1$ is greater than the second angle $\theta_2$. In some instances the first angle $\theta_1$ may be about 10° to about 35° or about 10° to about 30°, and the second angle $\theta_2$ may be about 5° to about 25° or about 5° to about 20°, for example.

The distal conical portion 46 may taper toward the central longitudinal axis X at a third angle $\theta_3$ in the first plane (FIG. 2) and the distal conical portion 46 may taper toward the central longitudinal axis X at a fourth angle $\theta_4$ in the second plane (FIG. 3) different from the third angle $\theta_3$. In the illustrated embodiment, the third angle $\theta_3$ is greater than the fourth angle $\theta_4$. In some instances the third angle $\theta_3$ may be about 20° to about 60° or about 25° to about 45°, and the fourth angle $\theta_4$ may be about 5° to about 30° or about 5° to about 25°, for example.

As shown in FIG. 2, the first angle $\theta_1$ may be less than the third angle $\theta_3$ in instances in which the first length $L_1$ is greater than the second length $L_2$, however, in other instances, the first angle $\theta_1$ may be greater than or equal to the third angle $\theta_3$. As shown in FIG. 3, the second angle $\theta_2$ may be less than the fourth angle $\theta_4$ in instances in which the first length $L_1$ is greater than the second length $L_2$, however, in other instances, the second angle $\theta_2$ may be greater than or equal to the fourth angle $\theta_4$. In some instances, the first angle $\theta_1$ may be greater than the fourth angle $\theta_4$, whereas in other instances, the first angle $\theta_1$ may be less than the fourth angle $\theta_4$.

The inflatable balloon 20 may have a non-circular cross-section, such as an elliptical cross-section, in a fully inflated configuration. In some instances the elliptical cross-section may have an ellipse shape, an oval shape, or flattened shape, for example. Accordingly, at a given plane perpendicular to the central longitudinal axis X the balloon 20 may extend away from the central longitudinal axis X a greater distance at a first location (e.g., antipodal points on a major axis of the balloon 20) than at a second location (e.g., antipodal points on a minor axis of the balloon 20) in an inflated configuration. For example, in a fully inflated configuration the proximal conical portion 42, the radially outermost extent 44, and/or the distal conical portion 46 may have elliptical cross-sections taken in planes perpendicular to the central longitudinal axis X and passing through the respective section of the balloon 20. It is noted that in instances in which the outer tubular member 30 and the inner tubular member 32 are cylindrical, the proximal waist 36 and the distal waist 38 may have a circular cross-section.

Figure 4:
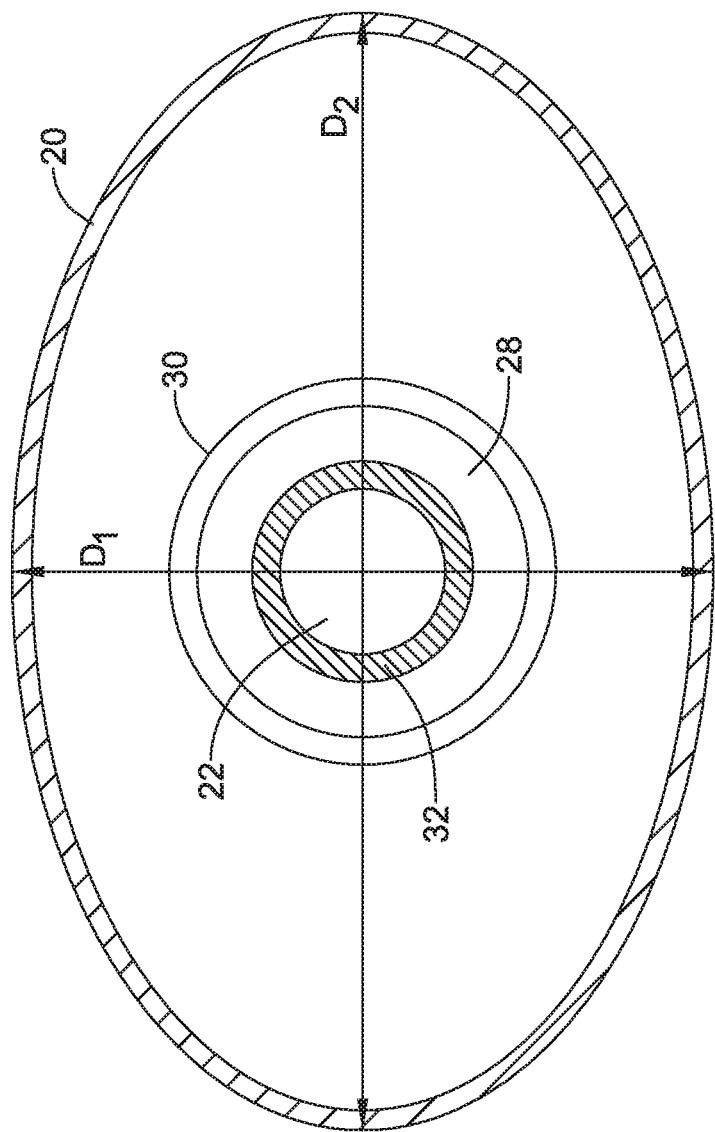
FIG. 4 is a transverse cross-sectional view taken along line 4-4 of FIGS. 2 and 3.
Figure 5:
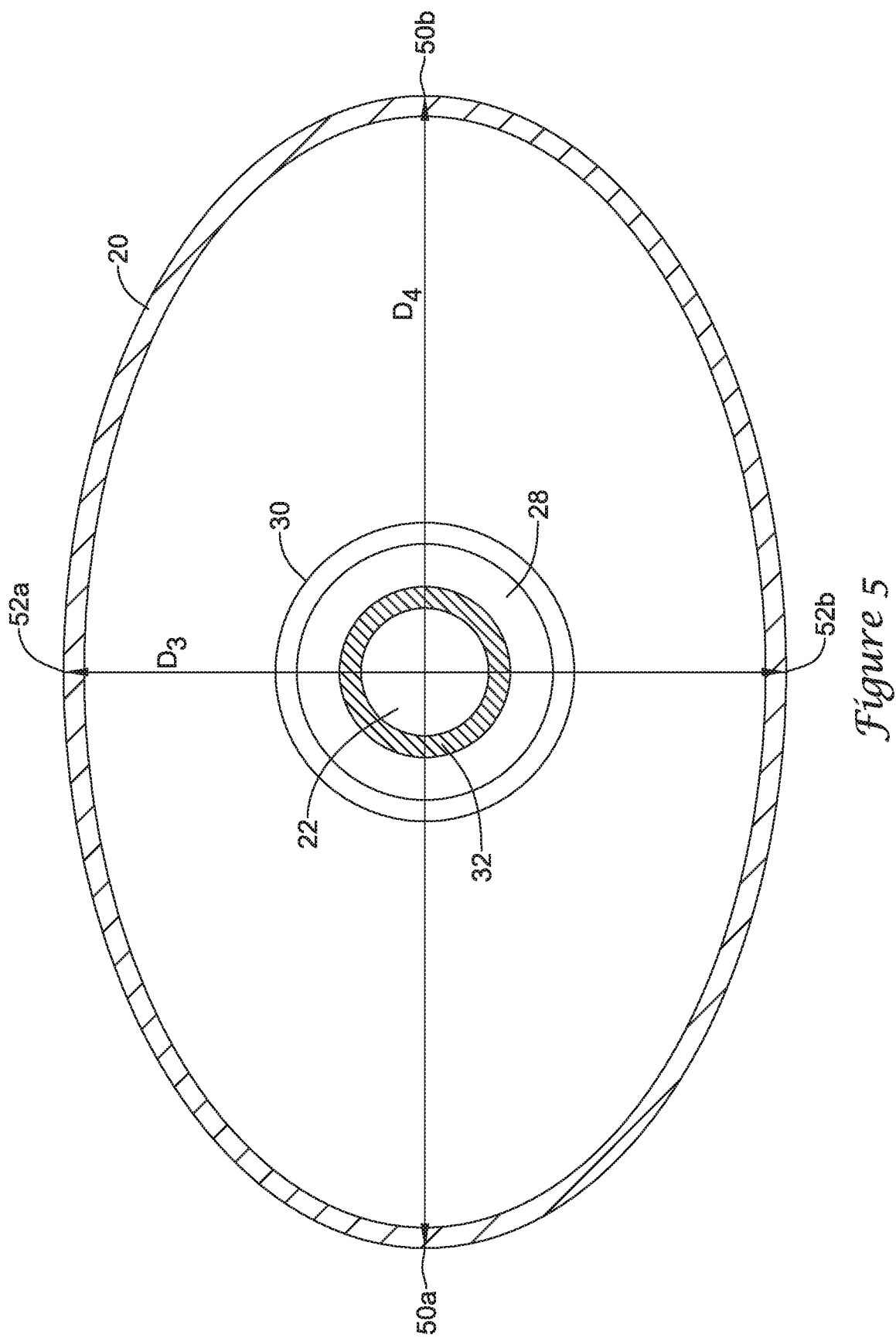
FIG. 5 is a transverse cross-sectional view taken along line 5-5 of FIGS. 2 and 3.
Figure 6:
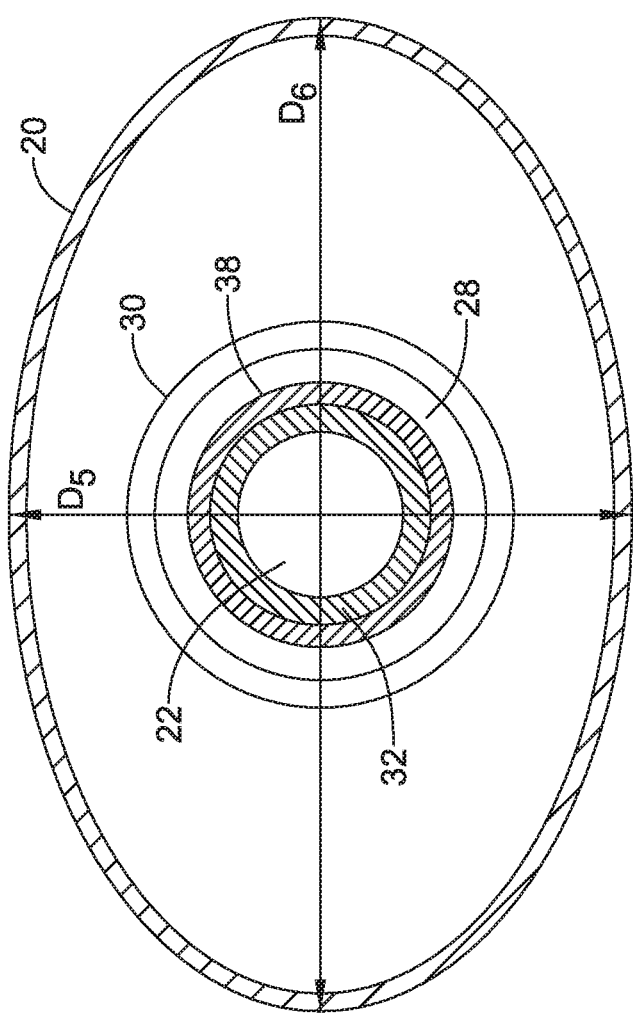
FIG. 6 is transverse cross-sectional view taken along line 6-6 of FIGS. 2 and 3.

FIG. 4, which is a transverse cross-sectional view taken along line 4-4 in FIGS. 2 and 3, shows the transverse cross-section of the inflatable balloon 20 in a plane perpendicular to the central longitudinal axis X of the catheter shaft 12 that passes through the proximal conical portion 42 of the balloon 20. FIG. 5, which is a transverse cross-sectional view taken along line 5-5 in FIGS. 2 and 3, shows the transverse cross-section of the inflatable balloon 20 in a plane perpendicular to the central longitudinal axis X of the catheter shaft 12 that passes through the radially outermost extent 44 of the balloon 20. FIG. 6, which is a transverse cross-sectional view taken along line 6-6 in FIGS. 2 and 3, shows the transverse cross-section of the inflatable balloon 20 in a plane perpendicular to the central longitudinal axis X of the catheter shaft 12 that passes through the distal conical portion 46.

As shown in FIG. 4, in a fully inflated configuration, the wall of the balloon 20 may be located a first distance $D_1$ from the central longitudinal axis X in a first direction taken in a plane perpendicular to the central longitudinal axis X that passes through the proximal conical portion 42, and the balloon 20 is located a second distance $D_2$ from the central longitudinal axis X in a second direction taken in the plane perpendicular to the central longitudinal axis X that passes through the proximal conical portion 42. The second direction is perpendicular to the first direction and the first distance $D_1$ is less than the second distance $D_2$. In some instances, the second distance $D_2$ may be 1.2 to 3, or about 1.2 to about 3, 1.5 to 3, or about 1.5 to about 3, 1.5 to 2.5, or about 1.5 to about 2.5, 1.5 to 2, or about 1.5 to about 2 times the first distance $D_1$, for example. In some instances the second distance $D_2$ may be about 1.2, 1.5, 1.7, 2.0, 2.2, 2.5 or 3 times the first distance $D_1$.

As shown in FIG. 5, in a fully inflated configuration, the wall of the balloon 20 is located a third distance $D_3$ from the central longitudinal axis X in a first direction taken in a plane perpendicular to the central longitudinal axis X that passes through the radially outermost extent 44, and the balloon 20 is located a fourth distance $D_4$ from the central longitudinal axis X in a second direction taken in the plane perpendicular to the central longitudinal axis X that passes through the radially outermost extent 44. The second direction is perpendicular to the first direction and the third distance $D_3$ is less than the fourth distance $D_4$. In some instances, the fourth distance $D_4$ may be 1.2 to 3, or about 1.2 to about 3, 1.5 to 3, or about 1.5 to about 3, 1.5 to 2.5, or about 1.5 to about 2.5, 1.5 to 2, or about 1.5 to about 2 times the third distance $D_3$, for example. In some instances the fourth distance $D_4$ may be about 1.2, 1.5, 1.7, 2.0, 2.2, 2.5 or 3 times the third distance $D_3$.

In the plane shown in FIG. 5, the elliptical cross-section of the fully inflated balloon 20 may have a major axis extending through antipodal points 50a, 50b (points that are diametrically opposite one another on the major axis) and a minor axis extending through antipodal points 52a, 52b (points that are diametrically opposite one another on the minor axis), wherein the major axis is perpendicular to the minor axis, and both the major axis and the minor axis are perpendicular to the central longitudinal axis X of the catheter shaft 12. The antipodal points 50a, 50b on the major axis may be a greater distance from the central longitudinal axis X than the antipodal points 52a, 52b on the minor axis.

As shown in FIG. 6, in a fully inflated configuration, the wall of the balloon 20 may be located a fifth distance $D_5$ from the central longitudinal axis X in a first direction taken in a plane perpendicular to the central longitudinal axis X that passes through the distal conical portion 46, and the balloon 20 is located a sixth distance $D_6$ from the central longitudinal axis X in a second direction taken in the plane perpendicular to the central longitudinal axis X that passes through the distal conical portion 46. The second direction is perpendicular to the first direction and the fifth distance $D_5$ is less than the sixth distance $D_6$. In some instances, the sixth distance $D_6$ may be 1.2 to 3, or about 1.2 to about 3, 1.5 to 3, or about 1.5 to about 3, 1.5 to 2.5, or about 1.5 to about 2.5, 1.5 to 2, or about 1.5 to about 2 times the fifth distance $D_5$, for example. In some instances the sixth distance $D_6$ may be about 1.2, 1.5, 1.7, 2.0, 2.2, 2.5 or 3 times the fifth distance $D_5$.

Figure 7:
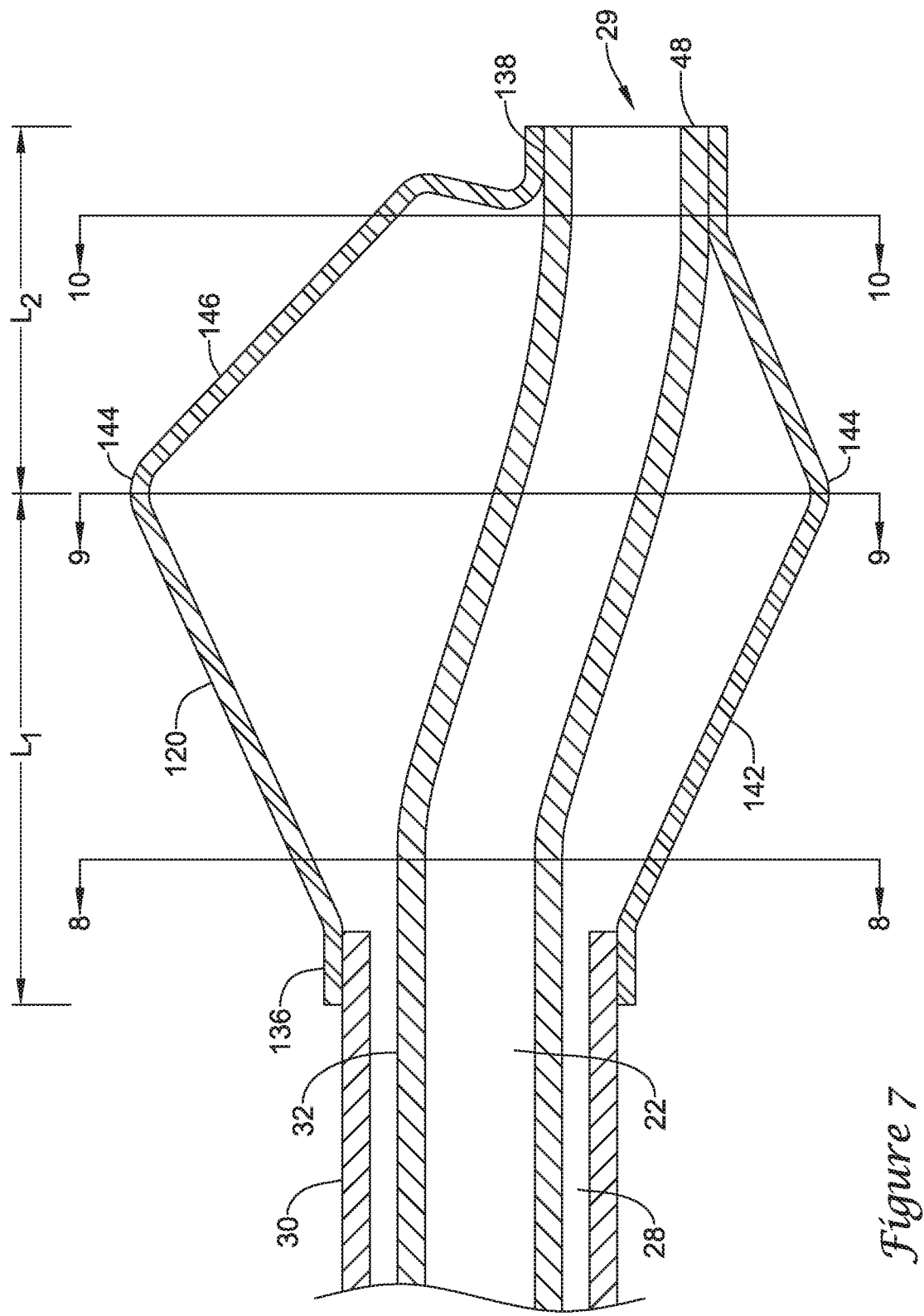
FIG. 7 is a longitudinal cross-sectional view of an alternative distal region of the balloon catheter of FIG. 1.

An alternative distal region of the catheter 10, including an inflatable balloon 120 secured to a distal end region of the catheter shaft 12, is illustrated at FIG. 7, which is a longitudinal cross-sectional view of the inflatable balloon 120 in a plane parallel to and passing through the central longitudinal axis of the catheter shaft 12. The balloon 120 may include a proximal waist 136 bonded, for example thermally bonded (e.g., laser, hot jaws) or adhesively bonded to a component of the catheter shaft 12. For example, the proximal waist 136 of the balloon 120 may be bonded or secured to the distal end of the outer tubular member 30. The balloon 120 may also include a distal waist 138 bonded, for example thermally bonded (e.g., laser, hot jaws) or adhesively bonded to a component of the catheter shaft 12. For example, the distal waist 138 of the balloon 120 may be bonded or secured to the distal end of the inner tubular member 32. The balloon 120 may only be secured to the catheter shaft 12 (e.g., inner tubular member 32 and outer tubular member 30) at the proximal and distal balloon waists 136, 138. The inflation lumen 28 extending through the catheter shaft 12 may be in fluid communication with the interior of the balloon 120.

The distal waist 138 may be secured to the distal end 48 of the inner tubular member 32 to form a distal tip. However, in other embodiments, the distal waist 138 may be inverted similar to the balloon 20 such that an inflatable portion of the balloon 120 is located at the distalmost extent of the catheter 10. The distal opening or port 29 of the guidewire lumen 22 be arranged at the distal tip of the catheter 10.

As shown in FIG. 7, at least a portion of the length of the portion of the catheter shaft 12 extending through the balloon 120 (e.g., the inner tubular member 32) may be non-centrally located (e.g., offset) within the balloon 120. For example, the portion of the catheter shaft 12 extending through the balloon 120 may be curved or angled, moving the portion of the catheter shaft 12 nearer to the wall of the balloon 120 on one side of the balloon 120 than to the wall of the balloon 120 on an opposite side of the balloon 120. The angle or curve of the portion of the catheter shaft 12 within the balloon 120 may further orient the distal opening 29 of the guidewire lumen 22 toward the true lumen of a blood vessel to facilitate the trajectory of a penetration member passing through the guidewire lumen 22 and out the distal opening 29 of the catheter shaft 12 into the true lumen of a blood vessel from a subintimal location.

The inflatable balloon 120 may have a generally conical shape in a fully inflated configuration. For example, the inflatable balloon 120 may have a proximal conical portion 142 that tapers away from the central longitudinal axis of the catheter shaft 12 in a distal direction from the proximal waist 136. The proximal conical portion 142 may taper radially outward from the central longitudinal axis of the catheter shaft 12 in a distal direction to a radially outermost extent 144 of the inflatable balloon 120. The inflatable balloon 120 may also have a distal conical portion 146 that tapers toward the central longitudinal axis of the catheter shaft 12 in a distal direction toward the distal waist 138, with the radially outermost extent 144 located between the proximal conical portion 142 and the distal conical portion 146.

The proximal conical portion 142 may have a first length $L_1$ measured along the central longitudinal axis of the catheter shaft 12 from the proximal waist 136 to the radially outermost extent 144 and the distal conical portion 146 may have a second length $L_2$ measured along the central longitudinal axis of the catheter shaft 12 from the radially outermost extent 144 to the distal tip 140. In some instances, the first length $L_1$ may be equal to the second length $L_2$, or the first length $L_1$ may be different from the second length $L_2$. For instance, the first length $L_1$ may be greater than or less than the second length $L_2$. In the illustrated embodiment, the first length $L_1$ is greater than the second length $L_2$, such that the outermost extent 144 of the inflatable balloon 120 is located closer to the distal tip 140 than the proximal waist 136 of the inflatable balloon 120.

The inflatable balloon 120 may have a non-circular cross-section, such as an elliptical cross-section, in a fully inflated configuration. In some instances the elliptical cross-section may have an ellipse shape, an oval shape, or flattened shape, for example. Accordingly, at a given plane perpendicular to the central longitudinal axis of the catheter shaft 12, the balloon 120 may extend away from the portion of the catheter shaft 12 (e.g., the inner tubular member 32) extending through the balloon 120 a greater distance at first locations (e.g., antipodal points on a major axis of the balloon 120) than at second locations (e.g., antipodal points on a minor axis of the balloon 120) in an inflated configuration. For example, in a fully inflated configuration the proximal conical portion 142, the radially outermost extent 144, and/or the distal conical portion 146 may have elliptical cross-sections taken in planes perpendicular to the central longitudinal axis of the catheter shaft 12 and passing through the respective section of the balloon 20. It is noted that in instances in which the outer tubular member 30 and the inner tubular member 32 are cylindrical, the proximal waist 136 and the distal waist 138 may have a circular cross-section.

Figure 8:
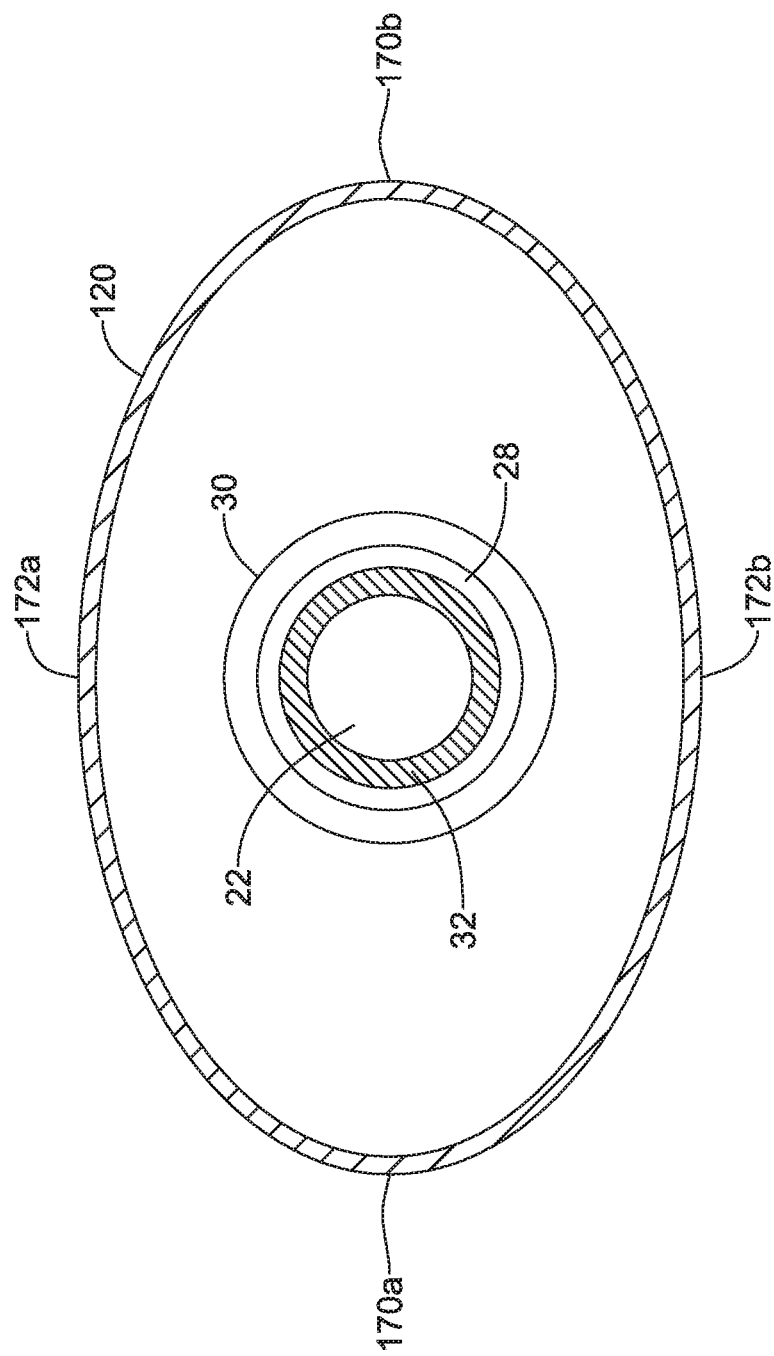
FIG. 8 is a transverse cross-sectional view taken along line 8-8 of FIG. 7.
Figure 9:
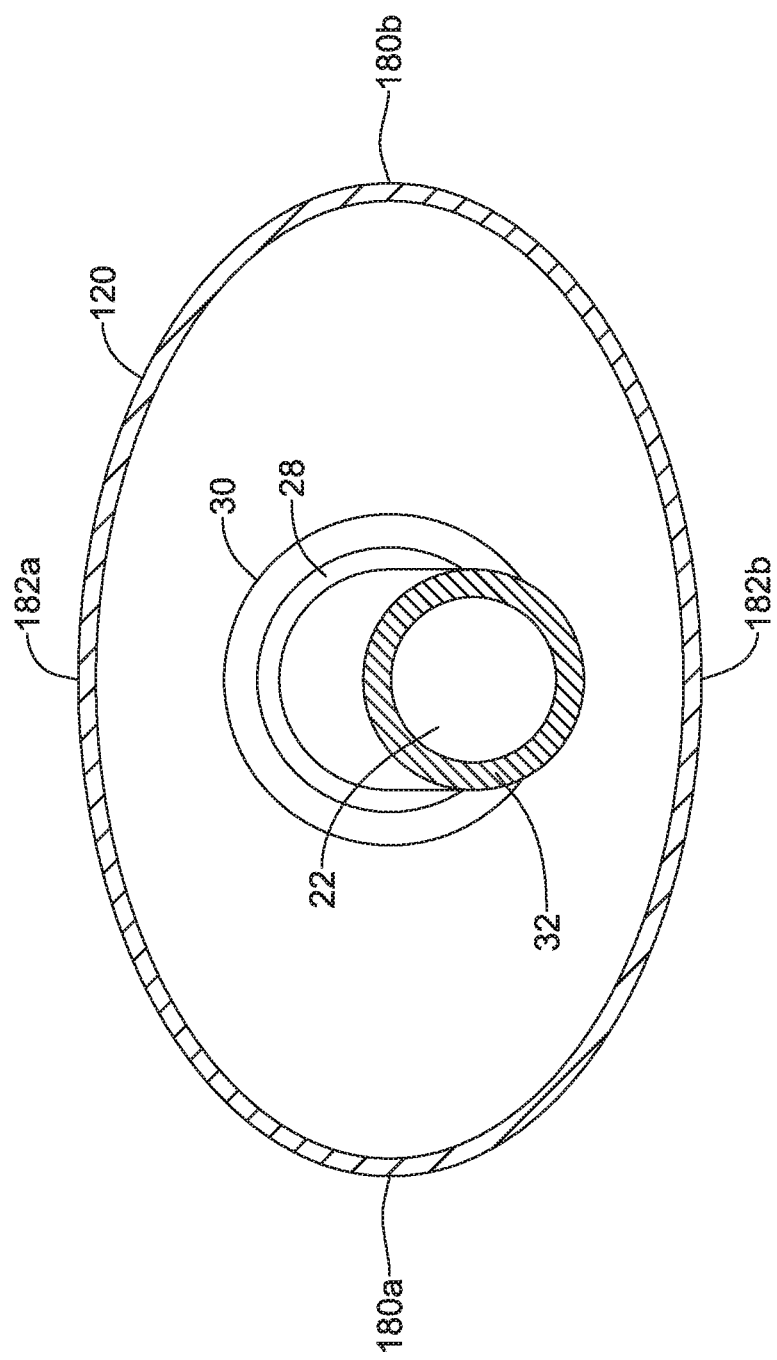
FIG. 9 is a transverse cross-sectional view taken along line 9-9 of FIG. 7.
Figure 10:
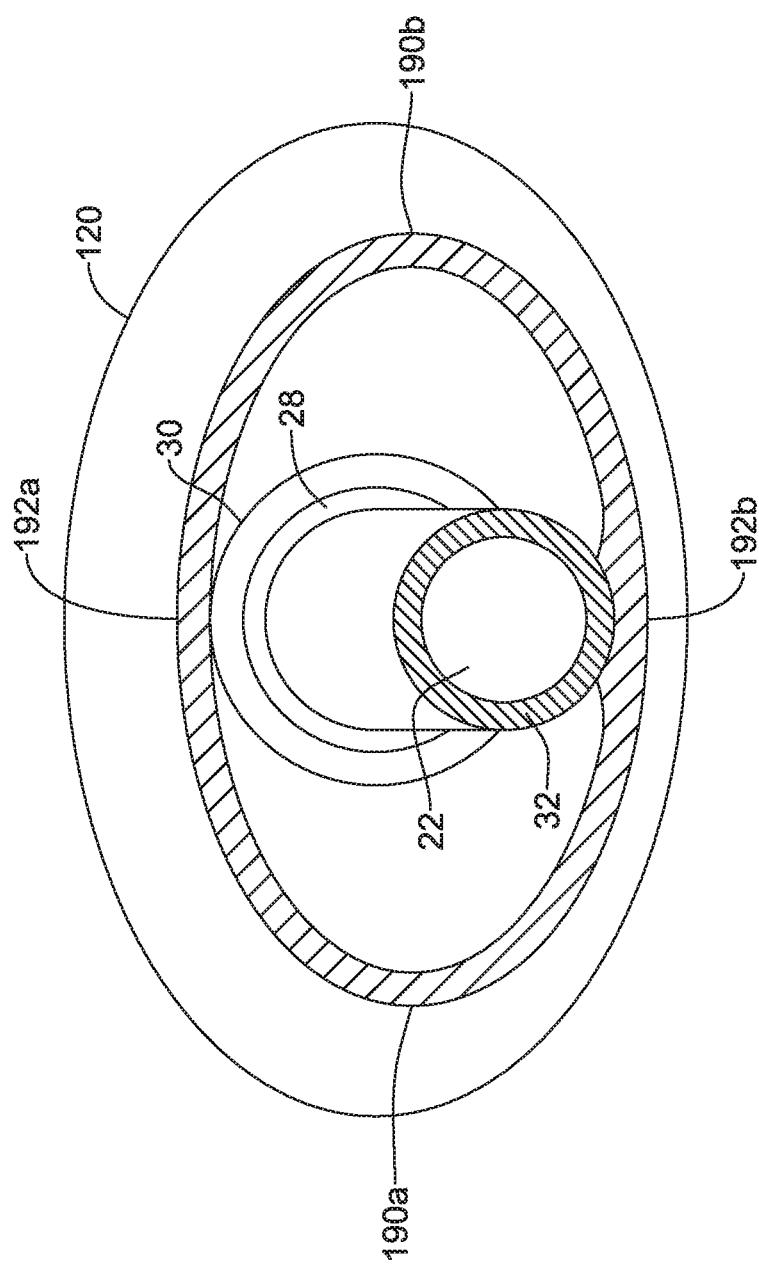
FIG. 10 is a transverse cross-sectional view taken along line 10-10 of FIG. 7.

FIG. 8, which is a transverse cross-sectional view taken along line 8-8 in FIG. 7, shows the transverse cross-section of the inflatable balloon 120 in a plane perpendicular to the central longitudinal axis of the catheter shaft 12 that passes through the proximal conical portion 142 of the balloon 120. FIG. 9, which is a transverse cross-sectional view taken along line 9-9 in FIG. 7, shows the transverse cross-section of the inflatable balloon 120 in a plane perpendicular to the central longitudinal axis of the catheter shaft 12 that passes through the radially outermost extent 144 of the balloon 120. FIG. 10, which is a transverse cross-sectional view taken along line 10-10 in FIG. 7, shows the transverse cross-section of the inflatable balloon 120 in a plane perpendicular to the central longitudinal axis of the catheter shaft 12 that passes through the distal conical portion 146.

As shown in FIG. 8, in a fully inflated configuration, within a plane perpendicular to the central longitudinal axis of the catheter shaft 12 that passes through the proximal conical portion 142 of the balloon 120 antipodal points 170a, 170b on the wall of the balloon 120 along a major axis of the balloon 120 (points that are diametrically opposite one another on the major axis) may be located a greater distance from the portion of the catheter shaft 12 (e.g., the inner tubular member 32) extending through the balloon 120 than antipodal points 172a, 172b on the wall of the balloon 120 along a minor axis of the balloon 120 (points that are diametrically opposite one another on the minor axis). The major axis being perpendicular to the minor axis. In some instances in which the portion of the catheter shaft 12 extending through the balloon 120 is not centrally oriented within the balloon 120, the wall of the catheter shaft 12 (e.g., the inner tubular member 32) may be positioned closer to the antipodal point 172b than the antipodal point 172a, while the wall of the catheter shaft 12 (e.g., the inner tubular member 32) may be equidistantly spaced between the antipodal points 170a, 170b.

As shown in FIG. 9, in a fully inflated configuration, within a plane perpendicular to the central longitudinal axis of the catheter shaft 12 that passes through the radially outermost extent 144 of the balloon 120 antipodal points 180a, 180b on the wall of the balloon 120 along a major axis of the balloon 120 (points that are diametrically opposite one another on the major axis) may be located a greater distance from the portion of the catheter shaft 12 (e.g., the inner tubular member 32) extending through the balloon 120 than antipodal points 182a, 182b on the wall of the balloon 120 along a minor axis of the balloon 120 (points that are diametrically opposite one another on the minor axis). The major axis being perpendicular to the minor axis. In some instances in which the portion of the catheter shaft 12 extending through the balloon 120 is not centrally oriented within the balloon 120, the wall of the catheter shaft 12 (e.g., the inner tubular member 32) may be positioned closer to the antipodal point 182b than the antipodal point 182a, while the wall of the catheter shaft 12 (e.g., the inner tubular member 32) may be equidistantly spaced between the antipodal points 180a, 180b.

As shown in FIG. 10, in a fully inflated configuration, within a plane perpendicular to the central longitudinal axis of the catheter shaft 12 that passes through the distal conical portion 146 of the balloon 120 antipodal points 190a, 190b on the wall of the balloon 120 along a major axis of the balloon 120 (points that are diametrically opposite one another on the major axis) may be located a greater distance from the portion of the catheter shaft 12 (e.g., the inner tubular member 32) extending through the balloon 120 than antipodal points 192a, 192b on the wall of the balloon 120 along a minor axis of the balloon 120 (points that are diametrically opposite one another on the minor axis). The major axis being perpendicular to the minor axis. In some instances in which the portion of the catheter shaft 12 extending through the balloon 120 is not centrally oriented within the balloon 120, the wall of the catheter shaft 12 (e.g., the inner tubular member 32) may be positioned closer to the antipodal point 192b than the antipodal point 192a, while the wall of the catheter shaft 12 (e.g., the inner tubular member 32) may be equidistantly spaced between the antipodal points 190a, 190b.

The balloon 20, 120 may be made from typical balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyether-ester, polyester, polyamide, elastomeric polyamides, polyether block amide (PEBA), as well as other suitable materials, or mixtures, combinations, copolymers thereof, polymer/metal composites, and the like. In some instances, the balloon 20 may include a single layer of material, whereas in other instances the balloon 20 may be of a multi-layer construction, including a plurality of layers of materials. For instance, the balloon 20 may be formed as a co-extrusion or tri-layer extrusion in some instances.

Figure 11:
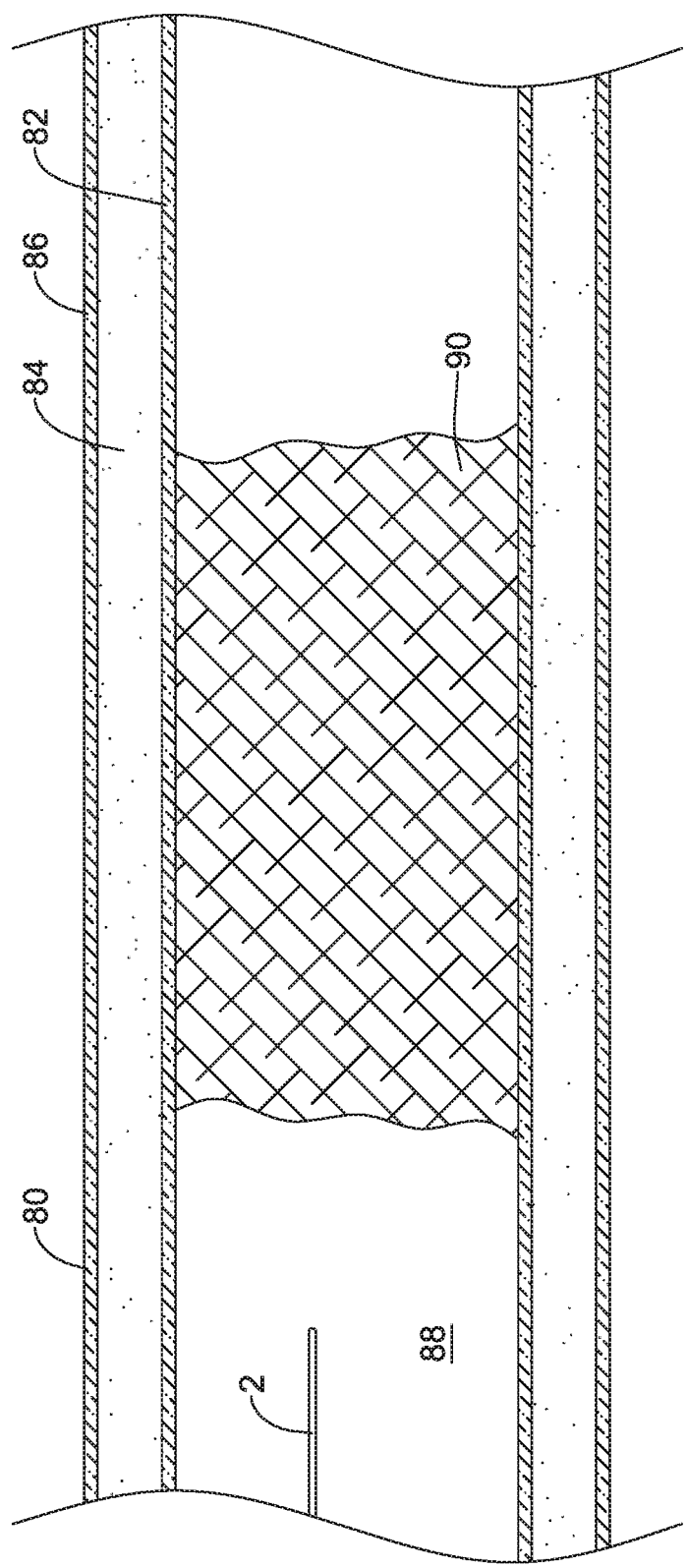
FIGS. 11-15 illustrate several aspects of an exemplary method for recanalizing an occluded blood vessel using the balloon catheter of FIG. 1.
Figure 12:
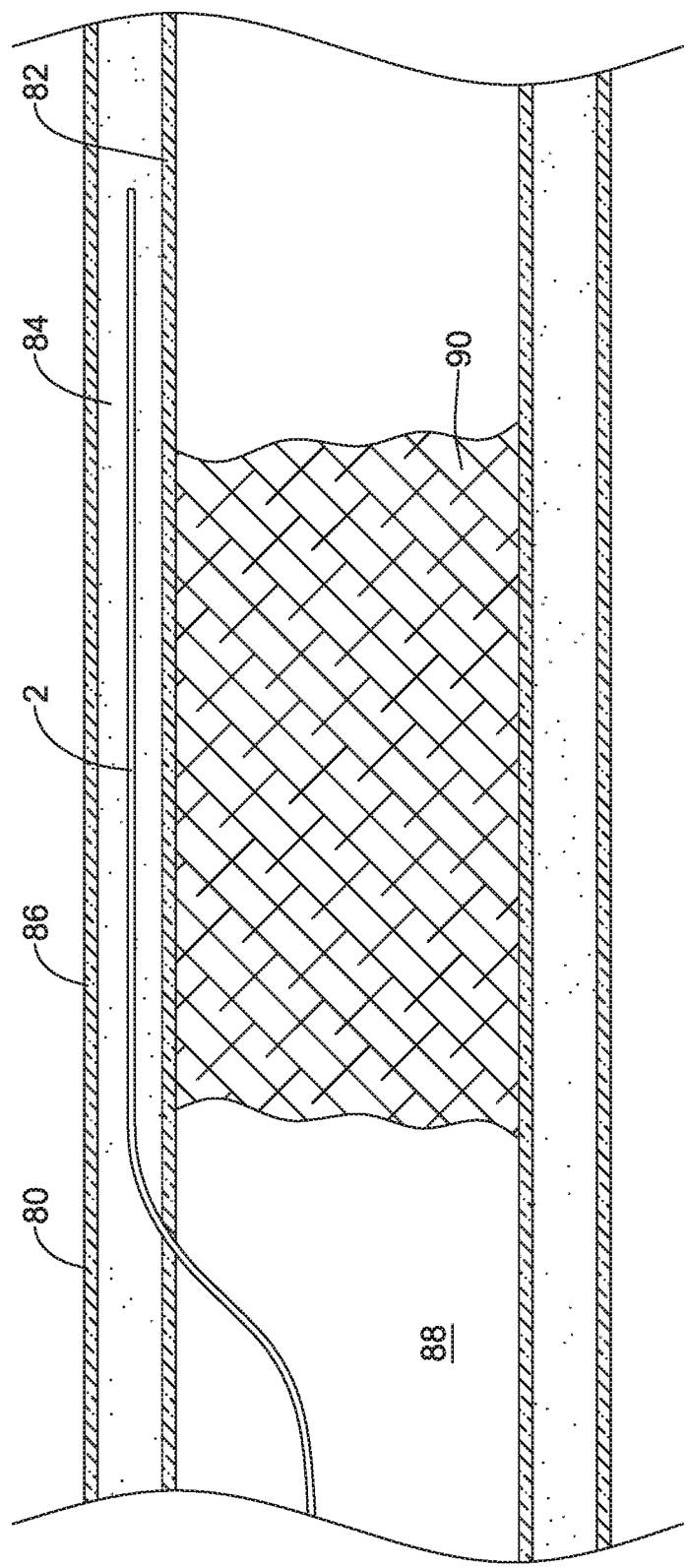

In some instances, it may be undesired, difficult or impossible to pass through an occlusion, such as a chronic total occlusion (CTO) in a lumen of a blood vessel with a medical device to recanalize the vessel. In such instances, it may be possible to recanalize the blood vessel through a subintimal approach using the catheter 10. Turning to FIGS. 11-16, several aspects of an exemplary method for recanalizing an occluded blood vessel using the catheter 10 are illustrated. As shown in FIG. 11, a guidewire 2 may initially be advanced through the lumen 88 of the vessel 80 to a location proximate a proximal end of an occlusion 90 blocking the lumen 88. The guidewire 2 may then be advanced to penetrate outward through the intima layer 82 at a location proximal of the proximal end of the occlusion 90 into the vessel wall 80. With the tip of the guidewire 2 located between the intima layer 82 and the adventitia layer 86, the guidewire 2 may be further advanced distally in a subintimal manner to create a subintimal space between the intima layer 82 and the adventitia layer 86. As shown in FIG. 12, the guidewire 2 may be advanced in a subintimal manner until the distal tip of the guidewire 2 is located distal of the distal end of the occlusion 90 in the subintimal space created, such as by dissection of the tissue layers of the vessel wall 80.

Figure 13:
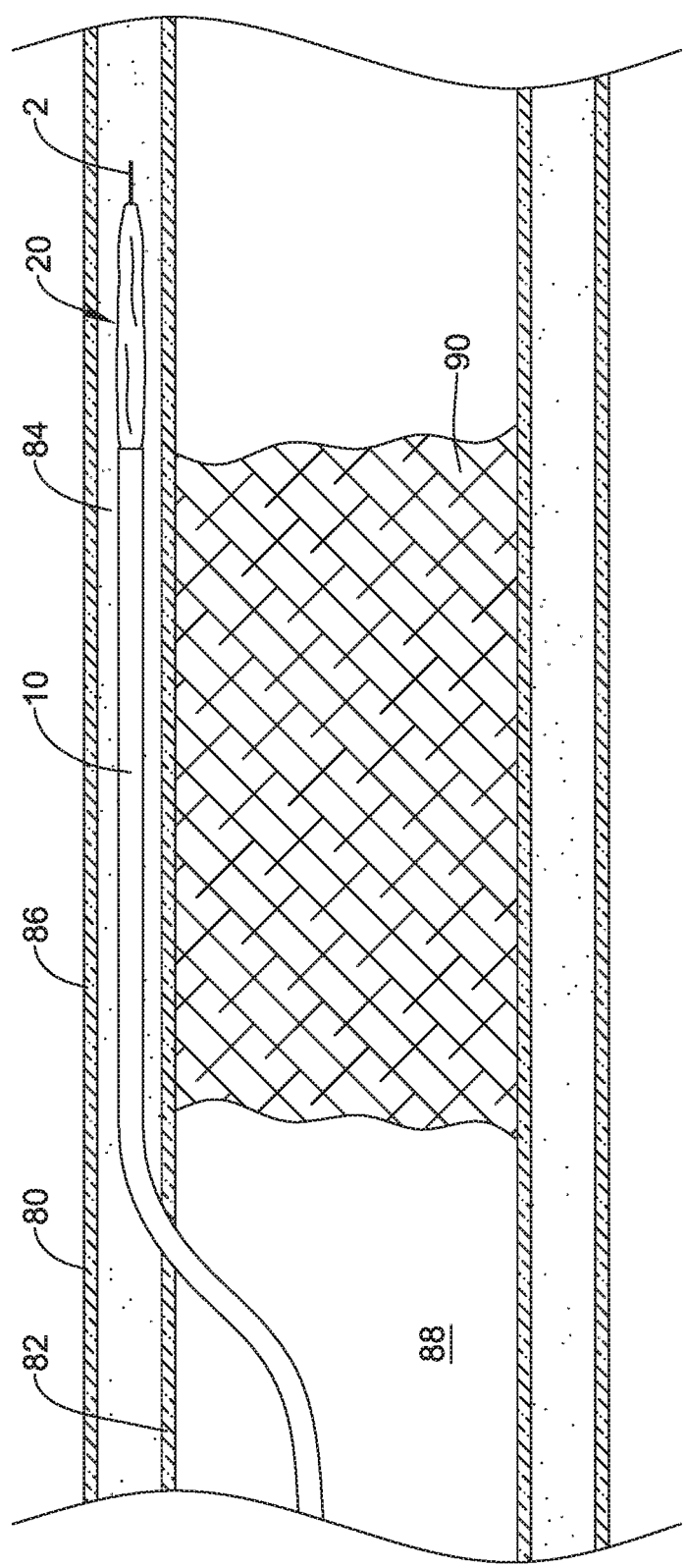

The recanalization catheter 10 may then be advanced distally over the guidewire 2 from the true lumen 88 proximal of the occlusion 90, into the subintimal space between the intima layer 82 and the adventitia layer 86, to a position in the subintimal space in which the distal portion of the catheter 10, including the inflatable balloon 20, is located distal of the distal end of the occlusion 90, as shown in FIG. 13. The recanalization catheter 10 may be advanced through the subintimal space in a delivery configuration, such as with the inflatable balloon 20 in a deflated configuration. It is noted that although the described procedure is illustrated with the inflatable balloon 20, the described procedure may be performed with the inflatable balloon 120, if desired.

With the inflatable balloon 20 positioned distal of the distal end of the occlusion 90, the guidewire 2 may be withdrawn proximally such that the distal tip of the guidewire 2 is located proximal of the inflatable balloon 20. In some instances, the guidewire 2 may be withdrawn completely from the guidewire lumen 22 of the catheter shaft 12, while in other instances the guidewire 2 may be retained in a proximal portion of the catheter shaft 12 proximal of the inflatable balloon.

Figure 14:
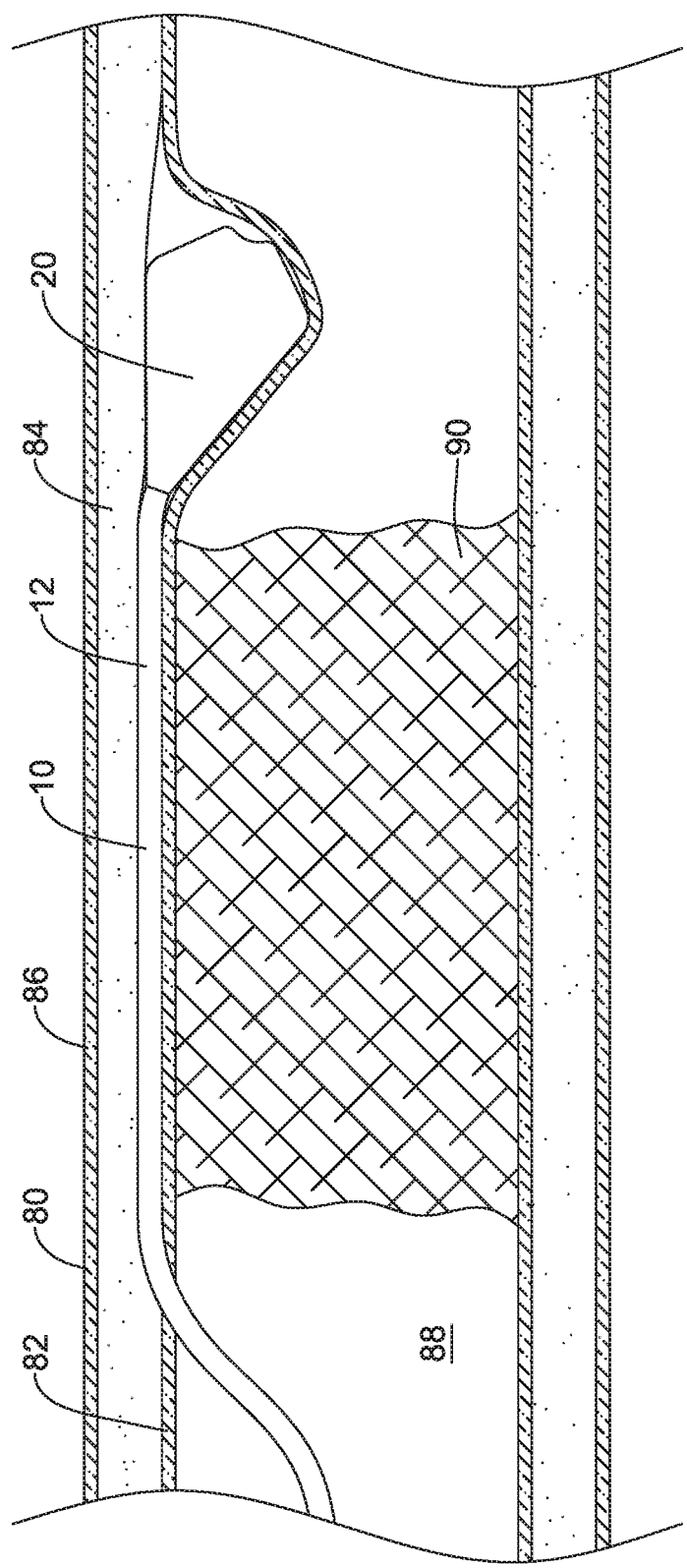

The inflatable balloon 20 may then be inflated to the fully inflated configuration in the subintimal space formed between the intima layer 82 and the adventitia layer 86, as shown in FIG. 14, by delivering an inflation fluid through the inflation lumen 28 of the catheter shaft 12 to the interior of the balloon 20. Inflating the inflatable balloon to or toward the fully inflated configuration may automatically cause the distal portion of the catheter shaft 12 that extends through the inflatable balloon 20 to deflect or bend toward the lumen 88 of the blood vessel 80 within the subintimal space to orient the distal opening 29 of the guidewire lumen 22 of the catheter shaft 12 toward the lumen 88.

When the inflatable balloon 20 is inflated, the distal opening 29 of the guidewire lumen 22 of the catheter shaft 12 may be oriented toward the lumen 88 such that a distal portion of a penetration member may be advanced distally out of the distal opening 29 to penetrate through the intima layer 82 into the lumen 88 of the blood vessel 80 distal of the occlusion 90.

Figure 15:
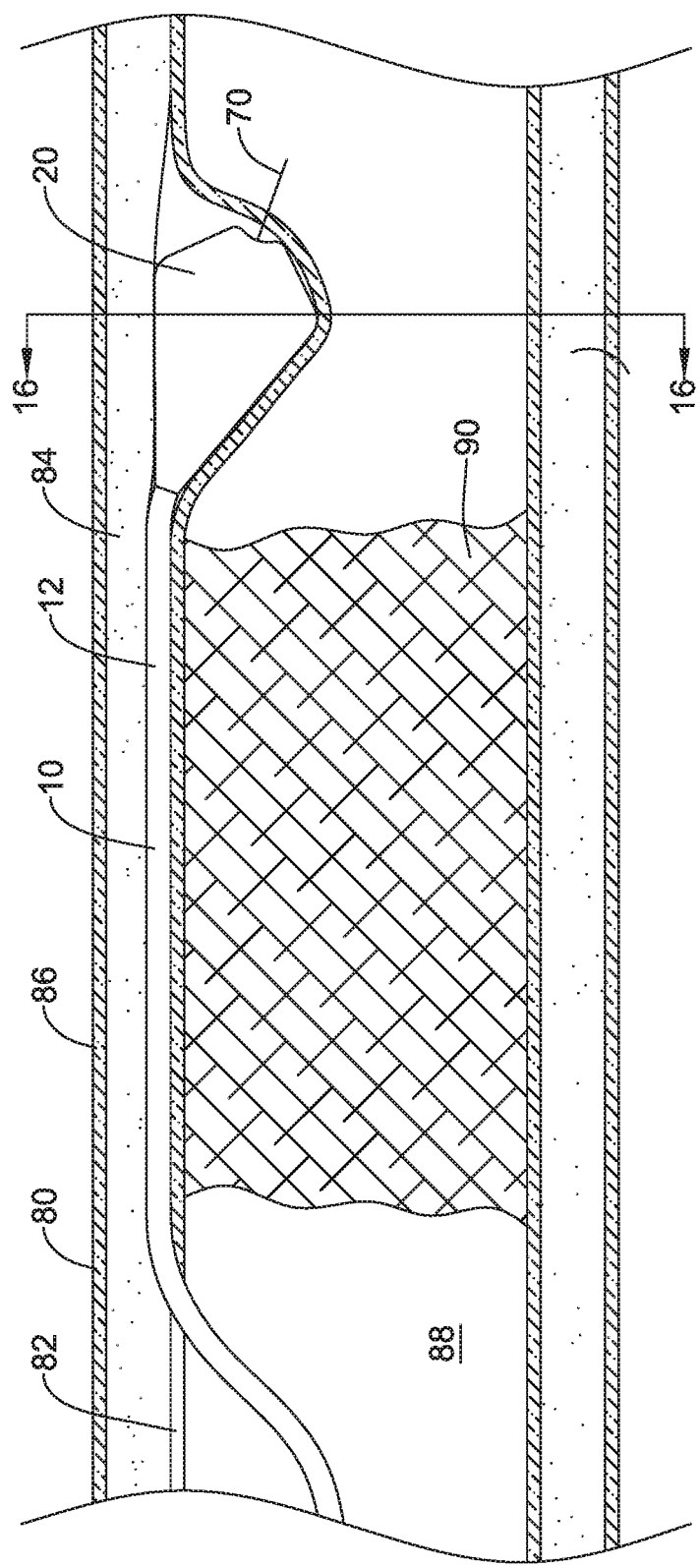

Once the inflatable balloon 20 is fully inflated and the distal portion of the catheter shaft 12 extending through the balloon 20 is deflected toward the lumen 88 such that the distal opening 29 of the guidewire lumen 22 is oriented toward the lumen 88, a penetration member 70, sized to be advanced through the guidewire lumen 22 of the catheter shaft 12, may be advanced through the guidewire lumen 22 and distally out of the distal opening 29 of the catheter shaft 12, as shown in FIG. 15. In some embodiments, the penetration member 70 may be the guidewire 2, or another guidewire introduced through the guidewire lumen 22 of the catheter shaft 12. In other embodiments, the penetration member 70 may be an elongate member, such as a needle cannula or stylet, having a sharpened distal tip configured to pierce through the intima layer 82 into the lumen 88 distal of the occlusion 90.

Figure 16:
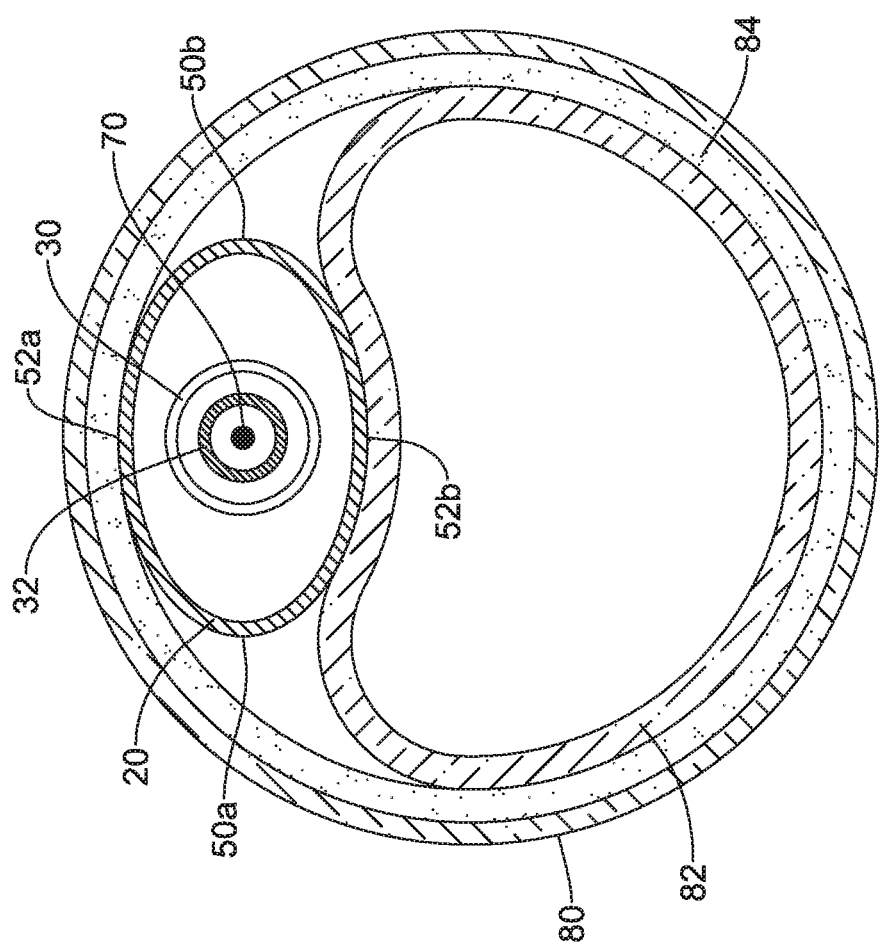
FIG. 16 is a cross-sectional view taken along line 16-16 of FIG. 15.

FIG. 16 is a cross-sectional view of the distal region of the catheter shaft 12 positioned in a subintimal space created between two tissue layers of the wall of the blood vessel 80. The blood vessel 80 typically has three tissue layers, an innermost layer or intima layer (i.e., tunica intima) 82, an intermediate layer or media layer (i.e., tunica media) 84, and an outermost layer or adventitia layer (tunica adventitia) 86, with the media layer 84 positioned between the intima layer 82 and the adventitia layer 86. The intima layer 82 is a layer of endothelial cells lining the lumen 88 of the vessel 80, as well as a subendothelial layer made up of mostly loose connective tissue. The media layer 84 is a muscular layer formed primarily of circumferentially arranged smooth muscle cells. The adventitia layer 86, which forms the exterior layer of the vessel wall 80 is formed primarily of loose connective tissue made up of fibroblasts and associated collagen fibers.

As shown in FIG. 16, when inflated in the subintimal space between the intima layer 82 and the adventitia layer 86 of the vessel wall 80, the inflatable balloon 20 may automatically be oriented in the orientation shown in FIG. 16 such that the minor axis of the balloon 20 passing through the antipodal points 52a, 52b may be generally aligned to pass through the lumen 88 of the blood vessel 80, while the major axis of the balloon passing through the antipodal points 50a, 50b may not pass through the lumen 88 of the blood vessel 80. Thus, the non-circular, elliptical shape of the inflatable balloon 20 may provide a preference in rotational orientation of the balloon 20, and thus the catheter shaft 12, Thus, the orientation of the minor axis of the balloon 20 in the fully inflated configuration reduce the overall radial distance from the center of the blood vessel 80 to the outer extent of the balloon 20.

In the event the penetration member 70 is a guidewire, the catheter 10 may be withdrawn while leaving the guidewire routed around the occlusion 90 via the subintimal pathway. In instances in which the penetration member 70 is a separate elongate member, such as a needle cannula or stylet, the penetration member 70 may be withdrawn and replaced with a guidewire. Thereafter, the catheter may be withdrawn while leaving the guidewire routed around the occlusion 90 via the subintimal pathway.

Once a pathway has been created around the occlusion 90 via a subintimal track, one or more additional medical devices may be advanced through the blood vessel 80 to enlarge the pathway and/or pass distally of the occlusion 90 to perform a further medical procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A balloon catheter comprising:
    a catheter shaft having a central longitudinal axis, a guidewire lumen and an inflation lumen extending therethrough; and
    an inflatable balloon bonded to a distal end region of the catheter shaft, the inflatable balloon having a proximal waist secured to the catheter shaft and a distal waist bonded to the catheter shaft;
    the inflatable balloon having a generally conical shape having a proximal conical portion that tapers radially outward in a distal direction from the proximal waist;
    wherein the proximal conical portion has an elliptical cross-section taken in a plane perpendicular to the central longitudinal axis that passes through the proximal conical portion; and
    wherein the elliptical cross-section of the proximal conical portion of the inflatable balloon has a center on the central longitudinal axis, a major axis passing through the center and perpendicular to the central longitudinal axis, and a minor axis passing through the center and perpendicular to the central longitudinal axis and the major axis, and the central longitudinal axis passes through the center of the inflatable balloon such that opposing outermost points of the balloon on opposing sides of the center on the major axis are equidistant from the central longitudinal axis and opposing outermost points of the balloon on opposing sides of the center on the minor axis are equidistant from the central longitudinal axis;

wherein the catheter shaft includes an inner tubular member defining the guidewire lumen and an outer tubular member extending around the inner tubular member, the inflation lumen defined between the inner tubular member and the outer tubular member;

wherein the proximal waist is bonded to a distal end region of the outer tubular member, and the distal waist is bonded to a distal end region of the inner tubular member;

wherein introduction of an inflation fluid into the inflatable balloon causes the proximal conical portion of the inflatable balloon to assume the elliptical cross-section in an inflated configuration.

2. The balloon catheter of claim 1, wherein the inflatable balloon has a distal conical portion and a radially outermost extent between the proximal conical portion and the distal conical portion, the distal conical portion having an elliptical cross-section taken in a plane perpendicular to the central longitudinal axis that passes through the distal conical portion.

3. The balloon catheter of claim 2, wherein the distal conical portion tapers radially inward in a distal direction toward the distal waist.

4. The balloon catheter of claim 3,
wherein the proximal conical portion has a first length measured along the central longitudinal axis from the proximal waist to the radially outermost extent and the distal conical portion has a second length measured along the central longitudinal axis from the radially outermost extent to a distal tip of the balloon; and
wherein the first length is greater than the second length.

5. The balloon catheter of claim 2, wherein the proximal conical portion tapers away from the central longitudinal axis at a first angle in a first plane parallel to and passing through the central longitudinal axis, and the proximal conical portion tapers away from the central longitudinal axis at a second angle in a second plane parallel to and passing through the central longitudinal axis, wherein the second plane is perpendicular to the first plane and the first angle is greater than the second angle.

6. The balloon catheter of claim 5, wherein the distal conical portion tapers toward the central longitudinal axis at a third angle in the first plane parallel to and passing through the central longitudinal axis, and the distal conical portion tapers toward the central longitudinal axis at a fourth angle in the second plane parallel to and passing through the central longitudinal axis, wherein the third angle is greater than the fourth angle.

7. The balloon catheter of claim 6, wherein the first angle is less than the fourth angle.

8. The balloon catheter of claim 6, wherein the first angle is greater than the fourth angle.

9. The balloon catheter of claim 2, wherein the balloon is located a first distance from the central longitudinal axis in a first direction taken in a plane perpendicular to the central longitudinal axis that passes through the radially outermost extent, and the balloon is located a second distance from the central longitudinal axis in a second direction taken in the plane perpendicular to the central longitudinal axis that passes through the radially outermost extent, wherein the second direction is perpendicular to the first direction and the first distance is less than the second distance.

10. The balloon catheter of claim 1, wherein the distal waist is an inverted distal waist bonded to the catheter shaft.

11. The balloon catheter of claim 1, wherein the inflatable balloon is only bonded to the catheter shaft at the proximal and distal waists.

12. The balloon catheter of claim 1, wherein a distalmost extent of the inflatable balloon is flush with or extends distal of a distal end of the catheter shaft in an inflated configuration.

13. The balloon catheter of claim 1, wherein in the inflated configuration only the inflation fluid exerts an outward force upon an inner surface of the inflatable balloon.

14. A subintimal recanalization catheter assembly for recanalizing a blood vessel having an occlusion in a lumen thereof, the catheter assembly comprising:
an elongate catheter shaft having a central longitudinal axis, the catheter shaft including:
an outer tubular member having a lumen extending therethrough; and
an inner tubular member having a lumen extending therethrough, the inner tubular member being disposed in the lumen of the outer tubular member; and
an inflatable balloon having a proximal waist fixedly attached to a distal end region of the outer tubular member and a distal waist fixedly attached to a distal end region of the inner tubular member, the inflatable balloon configured to be inflated from an uninflated configuration to an inflated configuration with an inflation fluid;
wherein a distalmost extent of the inflatable balloon is flush with or extends distal of a distal end of the catheter shaft in the inflated configuration;
wherein in the inflated configuration in which only the inflation fluid exerts an outward force upon an inner surface of the inflatable balloon, the inflatable balloon has an elliptical cross-section taken in a plane perpendicular to the central longitudinal axis that passes through the inflatable balloon; and
wherein the elliptical cross-section of the inflatable balloon has a center on the central longitudinal axis, a major axis passing through the center and perpendicular to the central longitudinal axis, and a minor axis passing through the center and perpendicular to the central longitudinal axis and the major axis, and the central longitudinal axis passes through the center of the inflatable balloon such that opposing outermost points of the balloon on opposing sides of the center on the major axis are equidistant from the central longitudinal axis and opposing outermost points of the balloon on opposing sides of the center on the minor axis are equidistant from the central longitudinal axis.

15. The subintimal recanalization catheter assembly of claim 14, wherein the inflatable balloon has a generally conical shape having a proximal conical portion that tapers away from the central longitudinal axis in a distal direction from the proximal waist.

16. The subintimal recanalization catheter assembly of claim 15, wherein the inflatable balloon has a distal conical portion and a radially outermost extent between the proximal conical portion and the distal conical portion.

17. The subintimal recanalization catheter assembly of claim 16, wherein the proximal conical portion has an elliptical cross-section taken in a plane perpendicular to the central longitudinal axis that passes through the proximal conical portion and the distal conical portion has an elliptical cross-section taken in a plane perpendicular to the central longitudinal axis that passes through the distal conical portion.

18. The subintimal recanalization catheter assembly of claim 16, wherein the distal conical portion tapers toward the central longitudinal axis in a distal direction toward the distal waist.

19. A balloon catheter comprising:
a catheter shaft having a central longitudinal axis, a guidewire lumen and an inflation lumen extending therethrough; and
an inflatable balloon secured to a distal end region of the catheter shaft, the inflatable balloon having a proximal waist bonded to the catheter shaft and a distal waist bonded to the catheter shaft;
the inflatable balloon having a generally conical shape having a proximal conical portion and a distal conical portion, wherein the proximal conical portion tapers radially outward in a distal direction from the proximal waist and wherein the distal conical portion tapers radially inward in a distal direction toward the distal waist;
wherein the proximal conical portion has an elliptical cross-section taken in a plane perpendicular to the central longitudinal axis that passes through the proximal conical portion;
wherein the distal conical portion has an elliptical cross-section taken in a plane perpendicular to the central longitudinal axis that passes through the distal conical portion;
wherein the inflatable balloon has a radially outermost extent between the proximal conical portion and the distal conical portion;
wherein the elliptical cross-section of the proximal conical portion of the inflatable balloon has a center on the central longitudinal axis;
wherein the elliptical cross-section of the distal conical portion of the inflatable balloon has a center on the central longitudinal axis;
wherein the catheter shaft includes an inner tubular member defining the guidewire lumen and an outer tubular member extending around the inner tubular member, the inflation lumen defined between the inner tubular member and the outer tubular member;
wherein the proximal waist is bonded to a distal end region of the outer tubular member, and the distal waist is bonded to a distal end region of the inner tubular member;
wherein introduction of an inflation fluid into the inflatable balloon causes the proximal conical portion of the inflatable balloon and the distal conical portion of the inflatable balloon to each assume its respective elliptical cross-section in an inflated configuration of the inflatable balloon.

20. The balloon catheter of claim 19, wherein in the inflated configuration only the inflation fluid exerts an outward force upon an inner surface of the inflatable balloon.

* * * * *